(12) United States Patent
Galbo et al.

(10) Patent No.: US 6,403,680 B1
(45) Date of Patent: Jun. 11, 2002

(54) BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

(75) Inventors: James Peter Galbo, Wingdale, NY (US); Nicola Lelli, Basel (CH); Valerio Borzatta, Bologna (IT); Jean-Pierre Wolf, Courtaman (CH); Michael Ackerman, deceased, late of New City, NY (US), by Jane Ackerman, representative; Piero Piccinelli, Sasso Marconi (IT); Ivan Orban, Basel (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/424,138
(22) PCT Filed: May 14, 1998
(86) PCT No.: PCT/IB98/00728
§ 371 (c)(1),
(2), (4) Date: Nov. 18, 1999
(87) PCT Pub. No.: WO98/54177
PCT Pub. Date: Dec. 3, 1998

(30) Foreign Application Priority Data

May 27, 1997 (EP) .............................................. 97810325
May 27, 1997 (EP) .............................................. 97810329

(51) Int. Cl.[7] .................................................. C08K 5/34
(52) U.S. Cl. ........................ 524/96; 524/100; 252/403; 544/198; 544/209; 544/212
(58) Field of Search ................................ 544/198, 209, 544/212; 252/403; 524/96, 100

(56) References Cited

U.S. PATENT DOCUMENTS 4,086,204 A    4/1978 Cassandrini et al. ....... 260/45.8

(List continued on next page.)

FOREIGN PATENT DOCUMENTS

EP          0053775          6/1982

(List continued on next page.)

OTHER PUBLICATIONS

Chem. Abstr. 97:183468d for EP 0053775 (1982).

Primary Examiner—Kriellion A. Sanders
(74) Attorney, Agent, or Firm—Tyler A. Stevenson; David R. Crichton

(57) ABSTRACT

A product obtained by
1) reacting a compound of the formula (α)

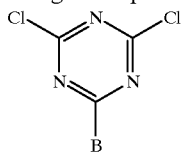

with a compound of the formula (β)

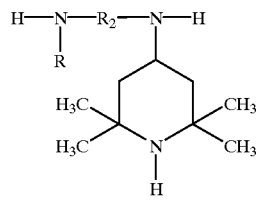

in a stoichiometric ratio to obtain a compound of the formula (γ)

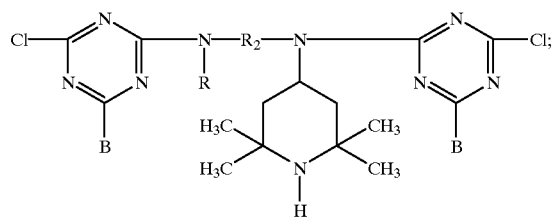

2) reacting the compound of the formula (β) with the compound of the formula (γ) in a molar ratio of 0.4:1 to 0.75:1;

3) reacting the end groups of the formula (δ)

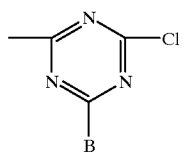

being present in the product of the reaction 2) with e.g. dibutylamine in a molar ratio of 2:1.7 to 2:3; the reactions 1) to 3) being carried out in an organic solvent in the presence of an inorganic base; and 4) transferring the groups of the formula

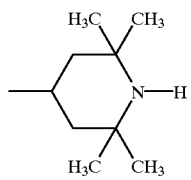

being present in the product of the reaction 3) to groups of the formula

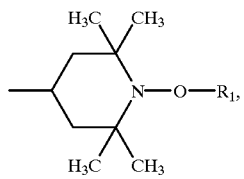

said transfer being carried out by reacting the product of the reaction 3) with a hydroperoxide in a hydrocarbon solvent in the presence of a peroxide decomposing catalyst; $R_1$ is in particular a hydrocarbyl radical, B is e.g. N-(2,2,6,6-tetramethyl-4-piperdyl)-butylamino, R is e.g. 2,2,6,6-tetramethyl-4-piperidyl and $R_2$ is e.g. hexamethylene.

31 Claims, 2 Drawing Sheets

U.S. PATENT DOCUMENTS

| | | | |
|---|---|---|---|
| 4,234,707 A | 11/1980 | Rody et al. | 525/437 |
| 4,331,586 A | 5/1982 | Hardy | 525/186 |
| 4,335,242 A | 6/1982 | Wiezer et al. | 544/198 |
| 4,459,395 A | 7/1984 | Cantatore | 524/100 |
| 4,492,791 A | 1/1985 | Orban et al. | 544/198 |
| 5,004,770 A | 4/1991 | Cortolano et al. | 524/99 |
| 5,096,950 A | 3/1992 | Galbo et al. | 524/99 |
| 5,124,378 A | 6/1992 | Behrens et al. | 524/95 |
| 5,204,473 A | 4/1993 | Winter et al. | 546/188 |
| 6,046,304 A | 4/2000 | Borzatta et al. | 528/423 |

FOREIGN PATENT DOCUMENTS

| | | |
|---|---|---|
| EP | 0309402 | 3/1989 |
| EP | 0357223 | 3/1990 |
| EP | 0376886 | 7/1990 |
| EP | 0377324 | 7/1990 |
| EP | 0389428 | 9/1990 |
| EP | 0435828 | 7/1991 |
| EP | 0462069 | 12/1991 |
| EP | 0782994 | 7/1997 |
| GB | 2301106 | 11/1996 |

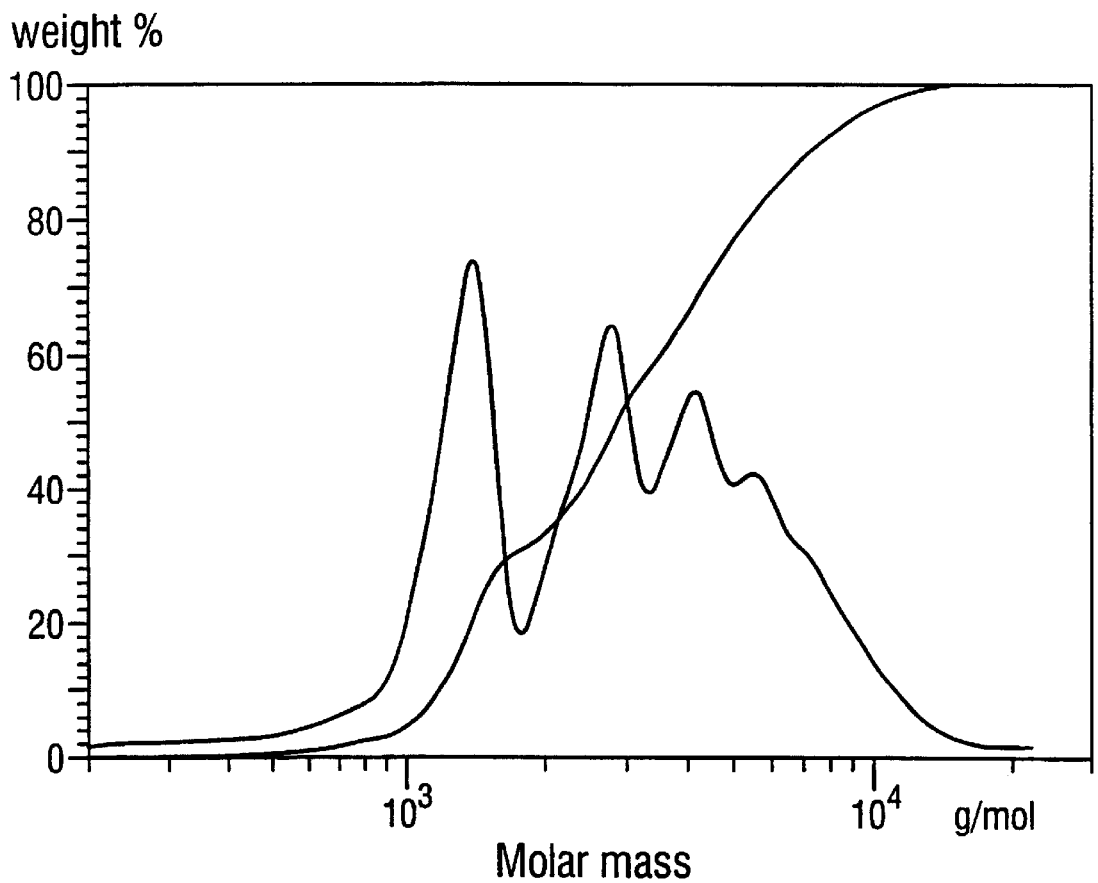

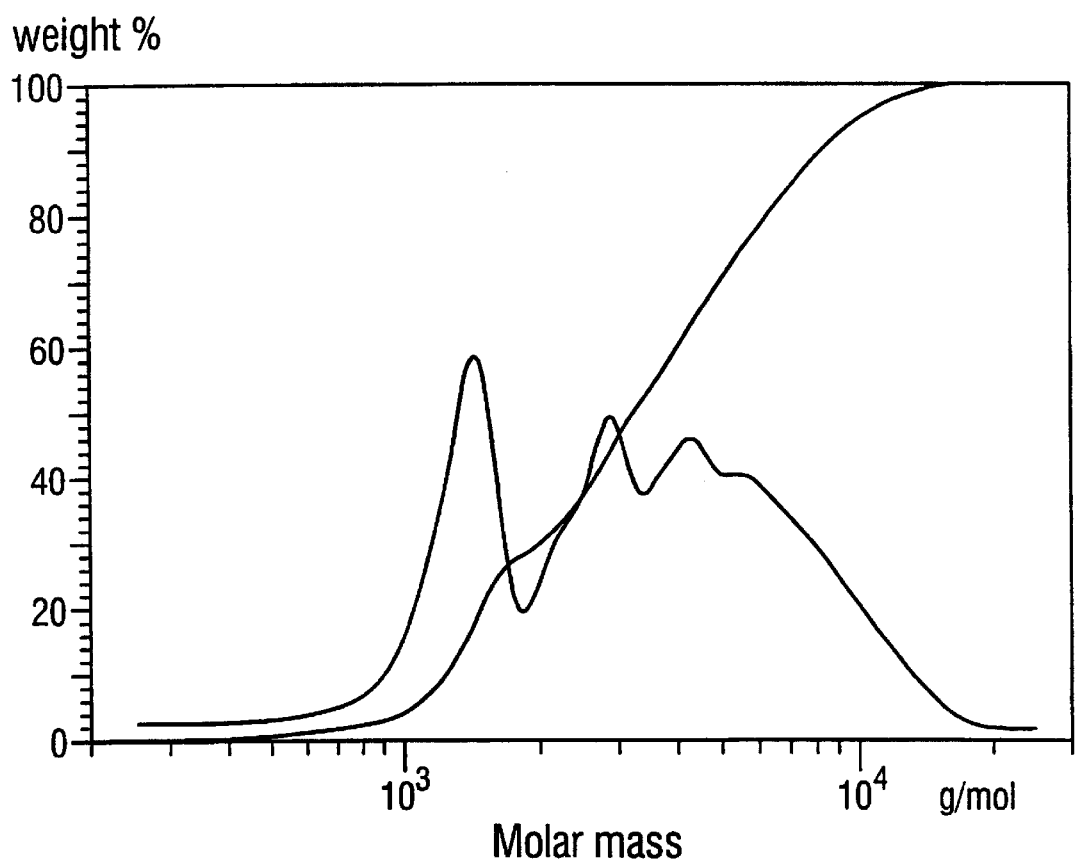

BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

The present invention relates to specific block oligomers containing 1-hydrocarbyloxy-2,2,6,6-tetramethyl-4-piperidyl groups, to their use as light stabilizers, heat stabilizers and oxidation stabilizers for organic materials, particularly synthetic polymers, and to the organic materials thus stabilized. The invention further relates to intermediate products.

The stabilization of synthetic polymers with derivatives of 2,2,6,6-tetramethylpiperidine has been described for example in U.S. Pat. No. 4,086,204, U.S. Pat. No. 4,331,586, U.S. Pat. No. 4,335,242, U.S. Pat. No. 4,234,707, U.S. Pat. No. 4,459,395, U.S. Pat. No. 4,492,791, U.S. Pat. No. 5,204,473, EP-A-53 775, EP-A-357 223, EP-A-377 324, EP-A-462 069, EP-A-782 994 and GB-A-2 301 106.

The present invention relates in particular to a product obtainable by 1) reacting a compound of the formula (α)

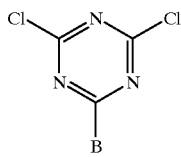

with a compound of the formula (β)

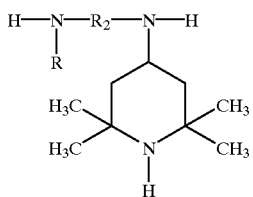

in a stoichiometric ratio to obtain a compound of the formula (γ);

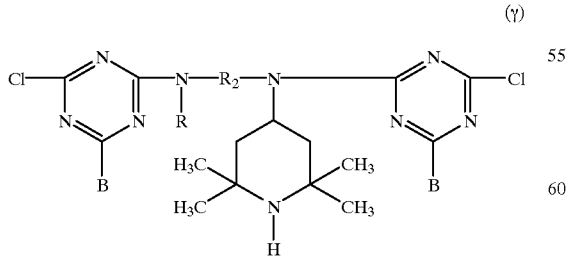

2) reacting the compound of the formula (β) with the compound of the formula (γ) in a molar ratio of 0.4:1 to 0.75:1, preferably 0.5:1 to 0.75:1, in particular 0.5:1;

3) reacting the end groups of the formula (δ)

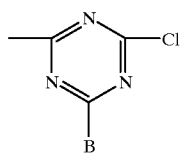

being present in the product of the reaction 2) with a compound of the formula (ε)

A—H    (ε)

in a molar ratio of 2 (end group):1.7 to 2:3, preferably 2:2 to 2:2.6, in particular 2:2 to 2:2.4;

the reactions 1) to 3) being carried out in an organic solvent in the presence of an inorganic base; and 4) transferring the groups of the formula (G-I)

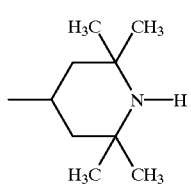

being present in the product of the reaction 3) to groups of the formula (G-II);

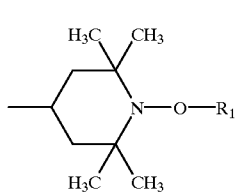

said transfer being carried out by reacting the product of the reaction 3) with a hydroperoxide in a hydrocarbon solvent in the presence of a peroxide decomposing catalyst;

$R_1$ is a hydrocarbyl radical or —O—R, is oxyl;
$R_2$ is $C_2$–$C_{12}$alkylene, $C_4$–$C_{12}$alkenylene, $C_1$–$C_7$cycloalkylene, $C_1$–$C_7$cycloalkylenedi($C_1$–$C_4$alkylene), $C_5$–$C_4$alkylenedi-($C_5$–$C_7$cycloalkylene), phenylenedi($C_5$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (I-a), (I-b) or (I-c);

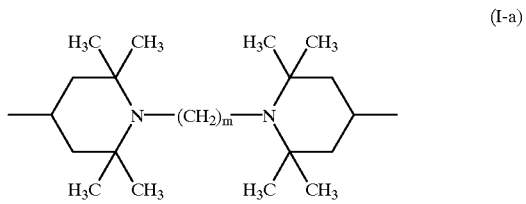

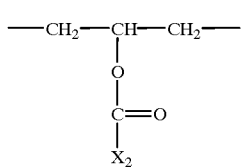
(I-b)

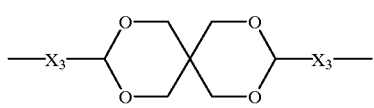
(I-c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

A is —$OR_3$, —$N(R_4)(R_5)$ or a group of the formula (II);

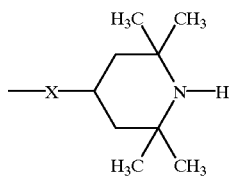
(II)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

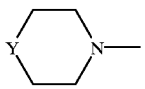
(III)

with Y being —O—, —$CH_2$—, —$CH_2CH_2$— or >N—$CH_3$;

and $R_3$ is additionally hydrogen or —$N(R_4)(R_5)$ is additionally a group of the formula (III);

X is —O— or >N—$R_6$;

$R_6$ is $C_1$–$C_{18}$alkyl, $C_3$–$C_{12}$alkenyl, $C_5$–$C_{18}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-I), or $C_2$–$C_4$alkyl which is substituted in the 2, 3 or 4 position by —OH, $C_1$–$C_8$alkoxy, di($C_1$–$C_4$alkyl)amino or a group of the formula (III);

R has one of the meanings given for $R_6$; and

B has one of the meanings given for A.

The transfer of the groups of the formula (G-I) to groups of the formula (G-II) may be carried out, for example, analogously to the method described in U.S. Pat. No. 4,921,962 which is incorporated by reference herein.

The meaning of $R_1$ depends on the hydrocarbon solvent used in the reaction 4). $R_1$ is preferably a hydrocarbyl radical having 5 to 18 carbon atoms.

$R_1$ is in particular $C_5$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent in the reaction 4) is accordingly, dependent on $R_1$, $C_5$–$C_{18}$alkane, $C_5$–$C_{18}$alkene, $C_5$–$C_{18}$alkynyl, $C_5$–$C_{12}$cycloalkane unsubstituted or substituted by $C_1$–$C_4$alkyl; $C_5$–$C_{12}$cycloalkene unsubstituted or substituted by $C_1$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

According to a further preferred embodiment $R_1$ is heptyl, octyl, cyclohexyl, methylcyclohexyl, cyclooctyl, cyclohexenyl, α-methylbenzyl or 1,2,3,4-tetrahydronaphthenyl, and the hydrocarbon solvent in the reaction 4) is, dependent on $R_1$, heptane, octane, cyclohexane, methylcyclohexane, cyclooctane, cyclohexene, ethylbenzene or tetralin.

According to a particularly preferred embodiment $R_1$ is octyl or cyclohexyl, and the hydrocarbon solvent in the reaction 4) is, dependent on $R_1$, octane or cyclohexane.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $R_1$ is preferably $C_6$–$C_{12}$alkyl, in particular heptyl or octyl. $R_4$, $R_5$ and $R_6$ are preferably $C_1$–$C_8$alkyl, in particular $C_1$–$C_4$alkyl.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3octoxypropyl and 4-methoxybutyl.

Examples of $C_2$–$C_4$alkyl substituted by di($C_1$–$C_4$alkyl) amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

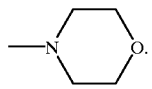

Preferred examples of $C_2$–$C_4$alkyl substituted by a group of the formula (III) are groups of the formula

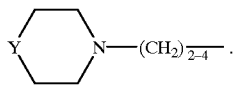

The group

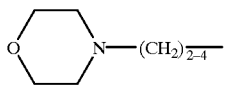

is particularly preferred.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

A preferred example of a bicyclic or tricyclic hydrocarbyl having 6 to 10 carbon atoms is 1,2,3,4-tetrahydronaphthenyl.

A preferred example of $C_5$–$C_{12}$cycloalkenyl unsubstituted or substituted by $C_1$–$C_4$alkyl is cyclohexenyl.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

An example of alkynyl is pentynyl or octynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of ($C_1$–$C_{12}$alkoxy)carbonyl are methoxycarbonyl, ethoxycarbonyl, propoxycarbonyt, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

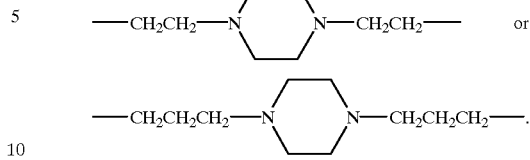

Examples of $C_4$–$C_{12}$alkylene interrupted by —O—, e.g. 1, 2 or 3 —O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,1 1-diyl and 4,7,10-trioxatridecane-1,13-diyl.

Examples of $C_4$–$C_{12}$alkylene interrupted by >N—$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

In the compound of the formula (γ), R is preferably a group of the formula (G-I).

Preferred is a product wherein
$R_2$ is $C_2$–$C_{12}$alkylene, $C_5$–$C_7$cyccloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—$X_1$ with $X_1$ being $C_1$–$C_{12}$acyl or ($C_1$–$C_{12}$alkoxy)carbonyl or having one of the definitions of $R_4$; or $R_2$ is a group of the formula (I-b);

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl;

and $R_3$ is additionally hydrogen or —N($R_4$)($R_5$) is additionally a group of the formula (III);

$R_6$ is $C_1$–$C_{18}$alkyl, $C_5$–$C_{12}$cycalalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (G-I).

Also preferred is a product wherein
$R_2$ is $C_2$–$C_{10}$alkylene, cyclohexylene, cyclohexylenedi($C_1$–$C_4$alkylene), $C_1$–$C_4$alkylene-dicyclohexylene or phenylenedi($C_1$–$C_4$alkylene), $R_3$, $R_4$ and $R_5$, which are identical or different, are $C_1$–$C_{12}$alkyl, $C_5$–$C_7$cycloalkyl which is unsubstituted or substituted by 1, 2 or 3 $C_1$–$C_4$alkyl; phenyl which is unsubstituted or substituted by 1, 2 or 3 $C_1$–$C_4$alkyl; benzyl which is unsubstituted or substituted on the phenyl by $C_1$–$C_4$alkyl; or —N($R_4$)($R_5$) is additionally a group of the formula (III); and $R_6$ is $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; or a group of the formula (G-I).

Further preferred is a product wherein $R_2$ is $C_2$–$C_8$alkylene;

$R_3$, $R_4$ and $R_5$ which are identical or different, are $C_1$–$C_8$alkyl, cyclohexyl which is unsubstituted or substituted by methyl; phenyl which is unsubstituted or substituted by methyl; benzyl or —N($R_4$)($R_5$) is additionally 4-morpholinyl; and $R_6$ is $C_1$–$C_8$alkyl, cyclohexyl which is unsubstituted or substituted by methyl; benzyl or a group of the formula (G-I).

Particularly preferred is a product wherein $R_1$ is octyl or cyclohexyl, and the hydrocarbon solvent in the reaction 4) is, dependent on $R_1$, octane or cyclohexane;

$R_2$ is $C_2$–$C_6$alkylene;

A is —N($R_4$)($R_5$) or a group of the formula (II);

$R_4$ and $R_5$, which are identical or different, are $C_1$–$C_8$alkyl;

or —N($R_4$)($R_5$) is additionally 4-morpholinyl;

X is >$NR_6$;

$R_6$ is $C_1$–$C_8$alkyl; and

B has one of the meanings given for A.

Also particularly preferred is a product wherein $R_1$ is octyl or cyclohexyl, and the hydrocarbon solvent in the reaction 4) is, dependent on $R_1$, octane or cyclohexane;

$R_2$ is $C_2$–$C_6$alkylene;

R is a group of the formula (G-I);

A is —N($R_4$)($R_5$);

$R_4$ and $R_5$, which are identical or different, are $C_1$–$C_8$alkyl;

B is a group of the formula (II);

X is >$NR_6$;

$R_6$ is $C_1$–$C_8$alkyl.

The organic solvent used in the reactions 1), 2) and 3) is in particular an aromatic hydrocarbon or an aliphatic ketone.

Examples of an aromatic hydrocarbon are toluene, xylene, trimethylbenzene, isopropylbenzene, diisopropylbenzene and t-butylbenzene.

Examples of an aliphatic ketone are methyl ethyl ketone, methyl butyl ketone, methyl isobutyl ketone, methyl amyl ketone, ethyl butyl ketone, di-n-propyl ketone, methyl hexyl ketone and ethyl amyl ketone. Essentially water-insoluble ketones are preferred.

Preferred solvents are toluene, xylene, methyl butyl ketone and methyl isobutyl ketone. Xylene and methyl isobutyl ketone are particularly preferred.

Examples of the inorganic base used in the present process are sodium hydroxide, potassium hydroxide, sodium carbonate and potassium carbonate. Sodium hydroxide is preferred.

The reactions 1) to 3) are preferably carried out in an inert atmosphere, in particular under nitrogen.

Depending on the solvent, reaction 1) is, for example, carried out at a temperature of 10° to 90° C., preferably 20° to 90° C., in particular 50° to 85° C.

Reaction 2) is conveniently carried out in a closed system at a temperature of, for example, 110° to 200° C., preferably 130° to 190° C., in particular 150° to 160° C. When heating the reaction mixture to the desired temperature, the pressure increases, since the reaction is carried out in a closed system. Because of the low boiling points of the solvents used, generally a pressure of 3 to 8 bar, e.g. 4 to 6 bar, is measured in the reactor.

Reaction 3) is also conveniently carried out in a closed system at a temperature of, for example, 110° to 180° C., preferably 130° to 170° C., in particular 140° to 160° C. Due to the high temperature, a pressure of normally 3 to 8 bar, e.g. 4 to 6 bar, is again measured in the reactor.

If desired, after completion of the reaction 3), the compound of the formula (e) and eventually unreacted starting materials can be eliminated from the final mixture by distillation or by using the usual purification techniques.

The product of the reaction 3) is conveniently isolated before the reaction 4) follows.

The peroxide decomposing catalyst used in the reaction 4) is, for example, a metal carbonyl, metal oxide, metal acetylacetonate or a metal alkoxide where the metal is selected from the groups IVb, Vb, VIb, VIIb and VII of the periodic table, preferably vanadium (III) acetylacetonate, cobalt carbonyl, chromium (VI) oxide, titanium (IV) isopropoxide, titanium tetrabutoxide, molybdenum hexacarbonyl, molybdenum trioxide and the like. The most preferred catalyst is $MoO_3$.

Suitable hydroperoxides are t-butyl hydroperoxide, t-amyl hydroperoxide, t-hexyl hydroperoxide, t-octyl hydroperoxide, ethylbenzene hydroperoxide, tetralin hydroperoxide or cumene (=isopropylbenzene) hydroperoxide. The most preferred hydroperoxide is t-butyl hydroperoxide.

In the reaction 4) 2 to 8 moles, preferably 3 to 6 moles, of the hydroperoxide, 0.001 to 0.1 mole, preferably 0.005 to 0.05 moles, of the peroxide decomposing catalyst and 5 to 30 moles, preferably 10 to 20 moles, of the hydrocarbon solvent are applied, for example, per mole of the hindered amine moiety of the formula (G-I)

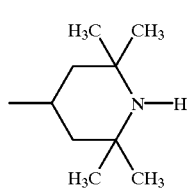

(G-I)

being present in the product of the reaction 3).

The transfer of the hindered amine moieties of the formula (G-I) to groups of the formula

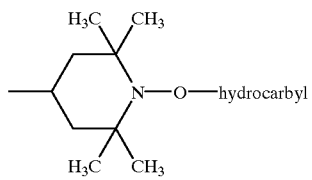

is, for example carried out at 75° to 160° C., preferably 100° to 150° C.

When in the reaction 4) the hindered amine moieties of the formula (G-I) are first treated with aqueous hydroperoxide in the presence of the peroxide decomposing catalyst in an insert organic solvent (for example analogously to the method described in U.S. Pat. No. 4,691,015), the initial reaction product obtained in a relatively short time is the corresponding N-oxyl intermediate (—$OR_1$=oxyl) which is highly colored and which can be isolated per se.

A further preferred embodiment of this invention relates therefore to a product obtainable according to the above reactions 1) to 4) wherein the radical —O—$R_1$, is oxyl and the hydrocarbon solvent in the reaction 4) is an inert organic solvent, preferably toluene or 1,2-dichloroethane.

When the organic solvent in the reaction 4) is a hydrocarbon having a labile hydrogen atom, when there remains a sufficient molar excess of hydroperoxide beyond that needed to convert the amine to the corresponding N-oxyl derivative, and when the reaction mixture is heated at moderate temperatures (preferably 100° to 150° C.) for an additional period, a further reaction takes place between the N-oxyl compound (either prepared in situ from the original amine or employed as the initial starting intermediate in the process) and the hydrocarbon solvent to give the corresponding N-hydrocarbyloxy derivative.

The original reaction mixture in the reaction 4) is colorless, but becomes highly colored as the N-oxyl intermediate is formed. This color disappears as the N-oxyl compound is converted into the colorless N-hydrocarbyloxy product. This process thus in essence has a built-in color indicator to show the extent of reaction. When the reaction mixture becomes colorless, it shows that the colored N-oxyl intermediate has been completely converted into the N-hydrocarbyloxy product.

An embodiment of this invention is also a product obtainable by hydrogenating the product of the reaction 4), wherein —OR$_1$ in the formula (G-II) is oxyl, to get a product with groups of the formula (G-III).

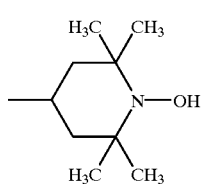

(G-III)

The hydrogenation is carried out according to known methods, for example in an organic solvent, e.g. methanol or ethanol, in the presence of a hydrogenation catalyst, preferably palladium on carbon or PtO$_2$, as described e.g. in U.S. Pat. No. 4,691,015.

If desired, the product obtained in reaction 4) can be purified by one of the following methods:

a) Residual peroxide is decomposed and solvent is evaporated to obtain a crude solid product. The solid is stirred with an inert solvent such as cyclohexane, octane, hexane, petroleum ether, xylene, toluene, acetone, methyl ethyl ketone, ethyl acetate, butyl acetate, t-butyl alcohol, t-amyl alcohol, isopropyl alcohol, ethanol, methanol, chloroform, dichloromethane, acetonitrile, diethyl ether, dibutyl ether and/or water. The mixture may be heated while stirring. After stirring, the mixture is cooled and the solid product is collected by filtration and dried.

b) Residual peroxide is decomposed and solvent is partially evaporated. The residue is filtered to obtain a solid which is washed with an inert solvent such as one of the above, which may be chilled, and then dried.

c) Residual peroxide is decomposed and solvent is evaporated at elevated temperature to obtain a melt. The warm melt is mixed with an inert solvent, such as one of the above, which may be chilled, and the resulting precipitate is collected by filtration and dried. Variations of this procedure include mixing the warm melt with solvent and then cooling the mixture to obtain a precipitate, or mixing the warm melt with solvent, heating to bring any solids into solution, and then cooling to obtain a precipitate.

d) Residual peroxide is decomposed and solvent is evaporated at elevated temperature to obtain a melt. The melt is dissolved in an inert solvent, such as one of the above, with or without heating, and the resulting solution may be concentrated by distilling off some of the excess solvent. The solution is then mixed with a second solvent, such as one of the above, at a temperature such that the product precipitates. The solid is collected by filtration and dried.

More Specifically, the Product Obtained in Reaction 4) is Preferably Purified as Follows:

After reaction 4) is complete, the crude reaction mixture is cooled to 50° C. and treated with 20% aqueous sodium sulfite until the concentration of residual peroxide falls below 0.5%. The aqueous layer is split off, and the organic layer is concentrated by heating the product solution at reduced pressure. The crude product is dissolved in excess t-butyl alcohol, and solvent is removed by heating the solution at reduced pressure until the concentration of solids is 50%. This solution is slowly added to cold methanol. The resulting precipitate is filtered, washed with methanol, and dried by heating under vacuum.

In general, the starting materials used in the above described process are known. In the case that they are not commercially available, they can be prepared analogously to known methods.

The compound of the formula (α) can be prepared, for example, by reacting cyanuric chloride with a compound B-H in a stoichiometric ratio in the presence of an organic solvent and an inorganic base. It is appropriate to use for the preparation of the compound of the formula (α) the same solvent and the same inorganic base as in the above indicated reactions 1) to 3).

If desired, after the preparation of the starting material of the formula (α), the reaction 1) can follow immediately without isolation of the compound of the formula (α).

Some starting materials of the formula (5) are, for example, described in WO-A-95/21 157, U.S. Pat. No. 4,316,837 and U.S. Pat. No. 4,743,688.

A further embodiment of this invention is a product obtainable by the above reactions 1)–3).

Products wherein the nitrogen atom in the group

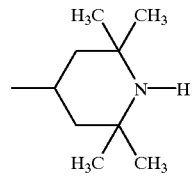

is substituted by $C_1$–$C_6$alkyl, $C_2$–$C_8$hydroxyalkyl, O, —OH, $C_1$–$C_{18}$hydrocarbyloxy (e.g. $C_1$–$C_{18}$alkoxy or $C_5$–$C_{12}$cycloalkoxy), —CH$_2$CN, $C_3$–$C_6$alkenyl, $C_3$–$C_6$alkynyl, $C_7$–$C_9$phenylalky which is unsubstituted or substituted on the phenyl by 1, 2 or 3 $C_1$–$C_4$alkyl; or $C_1$–$C_8$acyl, may be prepared in analogy to the above reactions 1) to 3), using the appropriate starting materials. The nitrogen atom is preferably substituted by $C_1$–$C_4$alkyl, in particular methyl.

Those starting materials which contain a group of the formula

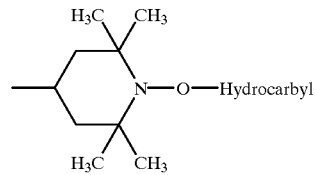

may be prepared, for example, analogously to the methods described in U.S. Pat. No. 4,921,962, U.S. Pat. No. 5,021,577 and U.S. Pat. No. 5,204,473.

The product of the reaction 3) is not a single specific compound but a compound with a molecular-weight distribution.

The polydispersity indicates the molecular-weight distribution of a polymeric compound. In the present application, the polydispersity is the ratio of weight-average ($\overline{M}w$) and numbel-average ($\overline{M}n$) molecular weights. A value of $\overline{M}w/\overline{M}n$ equal to 1 means that the compound is monodispers and has only one molecular weight and no molecular weight distribution. A narrow molecular weight distribution is characterized by a polydispersity ($\overline{M}w/\overline{M}n$) close to 1.

A preferred product of the reaction 3) has a polydispersity of 1.1 to 1.7, for example 1.1 to 1.6 or 1.3 to 1.7, in particular 1.3 to 1.6.

It is remarkable that the product of the reaction 3) contains, for example, less than 5 mol % in particular less than 2 mol % or less than 1 mol %, of linear by-products which are not end capped by a moiety of the formula

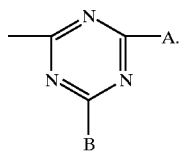

During the reactions 1) and 2) a cyclic compound of the formula

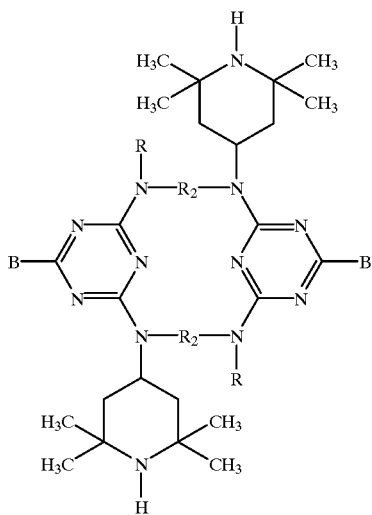

may be formed as by-product. That compound which is known from U.S. Pat. No. 4,442,250 may be present in an amount of, for example, less than 15 mol % in the product of the reaction 3).

The product of the reaction 3) is preferably a mixture containing a monodispers compound of the formula (M-I), a monodispers compound of the formula (M-II) and a monodispers compound of the formula (M-III), said compounds differing only in the number of the repetitive units,

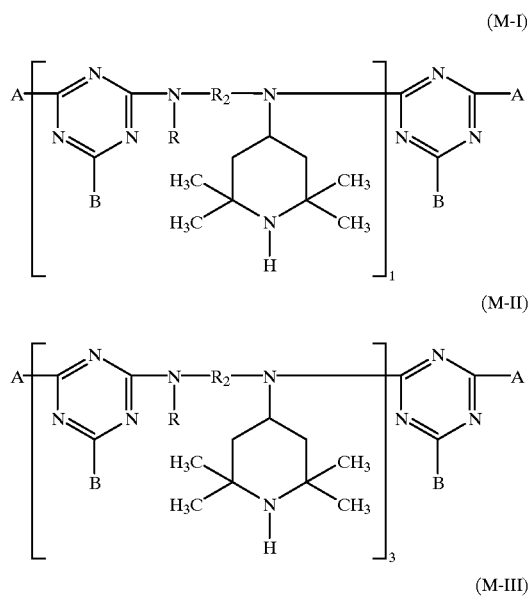

the radicals A, B, R and $R_2$ being as defined above and the total amount of the compound of the formula (M-I) being 15 to 45 mol %, e.g. 20 to 45 mol % or 25 to 45 mol % or 30 to 45 mol % or 30 to 40 mol %, the total amount of the compound of the formula (M-II) being 15 to 35 mol %, e.g. 15 to 30 mol % or 15 to 25 mol % or 20 to 25 mol %, and the total amount of the compound of the formula (M-III) being 3 to 18 mol %, e.g. 3 to 12 mol % or 5 to 12 mol %, relative to the total mixture (=100 mol %).

Preferred is a mixture which additionally contains a monodispers compound of the formula (M-IV)

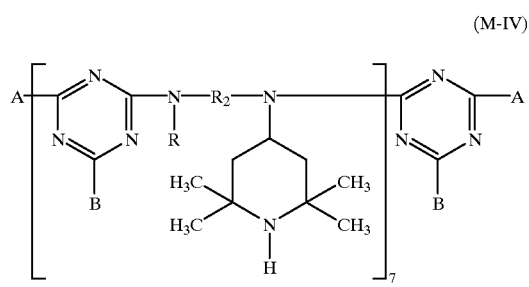

and wherein the total amount of the compound of the formula (M-IV) is 1 to 15 mol %, e.g. 1 to 10 mol % or 1 to 5 mol %, relative to the total mixture (=100 mol %).

Reaction 4) relates in particular to the transfer of the groups of the formula (G-I)

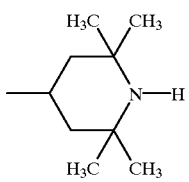

being present in the mixture containing the compounds of the formulae (M-I), (M-II), (M-III) and optionally (M-IV) to groups of the formula (G-II).

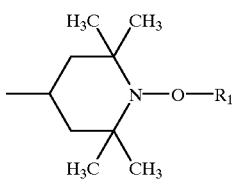

After the transfer the amounts of the below shown compounds of the formulae (P-I), (P-II), (P-II) and optionally (P-IV) in the product of the reaction 4) correspond to the amounts of the above shown initial compounds of the formulae (M-I), (M-II), (M-III) and optionally (M-IV), since the backbone of these compounds is not affected during the reaction.

Accordingly, a further embodiment of this invention is a mixture containing a monodispers compound of the formula (P-I), a monodispers compound of the formula (P-II) and a monodispers compound of the formula (P-III), said compounds differing only in the number of the repetitive units,

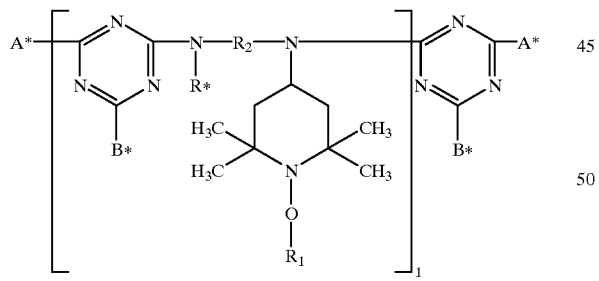

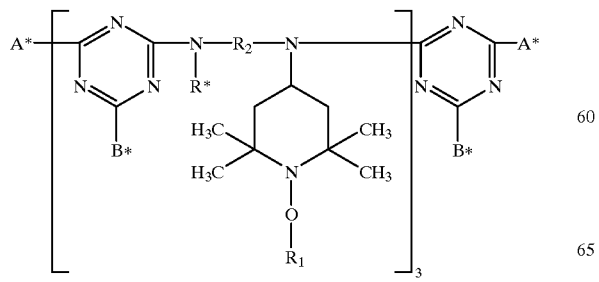

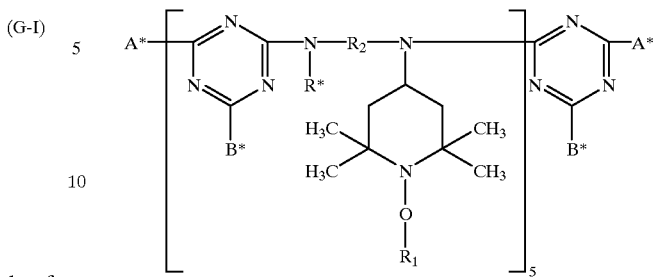

the total amount of the compound of the formula (P-I) being 15 to 45 mol %, e.g. 20 to 45 mol % or 25 to 45 mol % or 30 to 45 mol % or 30 to 40 mol %, the total amount of the compound of the formula (P-II) being 15 to 35 mol %, e.g. 15 to 30 mol % or 15 to 25 mol % or 20 to 25 mol % and the total amount of the compound of the formula (P-III) being 3 to 18 mol %, e.g. 3 to 12 mol % or 5 to 12 mol %, relative to the total mixture (=100 mol %), and $R_1$ is hydrogen, a hydrocarbyl radical or —O—$R_1$ is oxyl;

$R_2$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (I-a), (I-b) or (I-c);

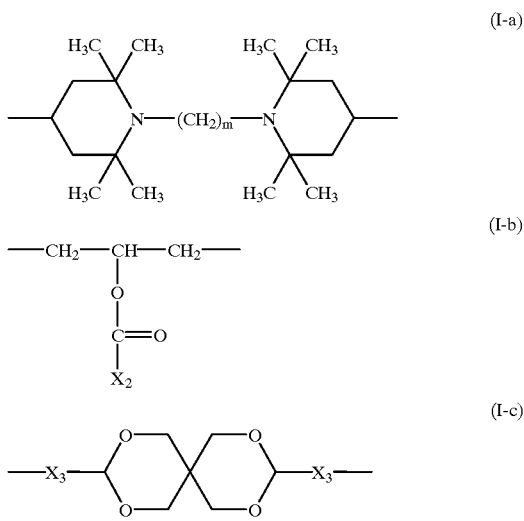

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

A* is —OR$_3$, —N(R$_4$)(R$_5$) or a group of the formula (G-IV);

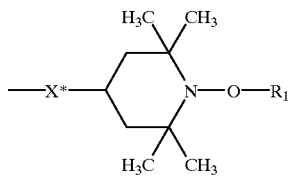

(G-IV)

R$_3$, R$_4$ and R$_5$, which are identical or different, are C$_1$–C$_{18}$alkyl, C$_5$–C$_{12}$cycloalkyl which is unsubstituted or substituted by 1, 2 or 3 C$_1$–C$_4$alkyl; C$_3$–C$_{18}$alkenyl, phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl; tetrahydrofurfuryl or C$_2$–C$_4$alkyl which is substituted in the 2, 3 or 4 position by —OH, C$_1$–C$_8$alkoxy, di(C$_1$–C$_4$alkyl)amino or a group of the formula (III);

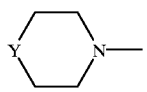

(III)

with Y being —O—, —CH$_2$—, —CH$_2$CH$_2$— or >N—CH$_3$;

and R$_3$ is additionally hydrogen or —N(R$_4$)(R$_5$) is additionally a group of the formula (III);

X* is —O— or >N—R$_6$*;

R$_6$* is C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (G-II),

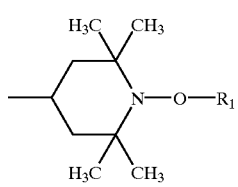

(G-II)

or C$_2$–C$_4$alkyl which is substituted in the 2, 3 or 4 position by —OH, C$_1$–C$_8$alkoxy, di(C$_1$–C$_4$alkyl)amino or a group of the formula (III);

R* has one of the meanings given for R$_6$*; and

B* has one of the meanings given for A*.

Preferred is a mixture which additionally contains a monodispers compound of the formula (P-IV)

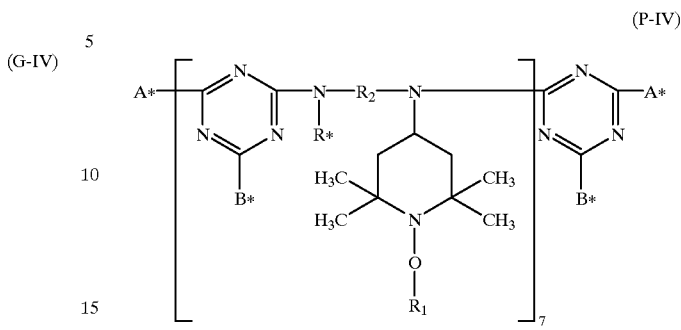

(P-IV)

wherein the radicals A*, B*, R*, R$_1$ and R$_2$ are as defined above and the total amount of the compound of the formula (P-IV) is 1 to 15 mol %, e.g. 1 to 10 mol % or 1 to 5 mol %, relative to the total mixture (=100 mol %).

Preferred are those mixtures, wherein

R$_1$ is octyl or cyclohexyl;

R$_2$ is C$_2$–C$_6$alkylene;

R* is a group of the formula (G-II);

A* is —N(R$_4$)(R$_5$);

R$_4$ and R$_5$, which are identical or different, are C$_1$–C$_8$alkyl;

B* is a group of the formula (G-IV);

X* is >NR$_6$*; and

R$_6$* is C$_1$–C$_8$alkyl.

In the mixtures according to this invention, the radical R$_1$ can act as a linking group between two or more compounds of the formulae (P-I), (P-II), (P-III) and/or (P-IV). In this case, bridges of the formula (L-I) are formed (L-I)

between the indicated compounds.

The meaning of R$_1$ can be deduced from the meaning of R$_1$. The only difference between these two radicals is that R$_1$* has one or two additional valences. Thus, R$_1$ as cyclohexyl corresponds to R$_1$* as cyclohexanediyl or cyclohexanetriyl and R$_1$ as octyl corresponds to R$_1$* as octanediyl or octanetriyl.

The products of this invention as well as the described mixtures are very effective in improving the light, heat and oxidation resistance of organic materials, especially synthetic polymers and copolymers. In particular, a low pigment interaction as well as a very good colour is observed in polypropylene, especially polypropylene fibres, in particular in the presence of flame retardants as well as in low density polyethylene (LDPE) films for agricultural use. It is further remarkable that the product of this invention as well as the described mixtures are flame retardants themselves.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbomene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated.

These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (—Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HIDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acryiic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrenelacrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylenelpropylene/diene terpolymer; and block copolymers of styrene such as styrene/butadiene/styrene, styrene/isoprene/styrene, styrene/ethylene/butylene/styrene or styrene/ethylene/propylene/ styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloridelyinyl acetate or vinylidene chloride/vinyl acetate copolymers.

9. Polymers derived from α,β-unsaturated acids and derivatives thereof such as polyacrylates and polymethacrylates; polymethyl methacryiates, polyacrylamides and polyacrylonitriles, impact-modified with butyl acrylate.

10. Copolymers of the monomers mentioned under 9) with each other or with other unsaturated monomers, for example acrylonitrilel butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 619, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or polym-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenovformaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without: accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVCICPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and a product or a mixture according to this invention.

The organic material is preferably a synthetic polymer, more particularly one selected from the aforementioned groups. Polyolefins are preferred and polyethylene and polypropylene are particularly preferred.

A further embodiment of this invention is a method for stabilizing an organic material against degradation induced by light, heat or oxidation, which comprises incorporating into said organic material a product or a mixture according to this invention.

The product or the mixture according to this invention can be used in various proportions depending on the nature of the material to be stabilized, on the end use and on the presence of other additives.

In general, it is appropriate to use, for example, 0.01 to 5% by weight of the product or the mixture according to this invention, relative to the weight of the material to be stabilized, preferably 0.05 to 2%, in particular 0.05 to 1%.

The product or the mixture according to this invention can be added, for example, to the polymeric materials before, during or after the polymerization or crosslinking of the said materials. Furthermore, they can be incorporated in the polymeric materials in the pure form or encapsulated in waxes, oils or polymers.

In general, the product or the mixture according to this invention can be incorporated in the polymeric materials by various processes, such as dry mixing in the form of powder, or wet mixing in the form of solutions or suspensions or also in the form of a masterbatch which contains the product or the mixture according to this invention in a concentration of 2.5 to 25 % by weight; in such operations, the polymer can be used in the form of powder, granules, solutions, suspensions or in the form of latices.

The materials stabilized with the product or the mixture according to this invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the product or the mixture according to this invention.

Particular examples of said conventional additives are:
1. Antioxidants
1.1 Alkylated monoghenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4, 6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4dioctylthiomethyl-6ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-ten-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis( 4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methyl-lenebis(2,6-di-tert-butylphenol), 4,4'-methylenebis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3n-dodecyimercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl3-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzyimercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl4-hydroxy-5-methylbenzyl)-malonate, didodecylmercaptoethyl-2,2-bis-(3,5-di4ert-butyl-4-hydroxybenzyl)malonate, bis[4-(1,1,3,3-tetramethylbutyl)phenyl]-2,2-bis(3,5-di-tert-butyl4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3, 5-triazine, 2-octylmercapto4,6-bis(3,5-di-tert-butyl-4-hydroxyanilino)-1,3,5-triazine, 2-octylmercapto-4,6-bis(3, 5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl- 4-hydroxyphenylpropionyl)-hexahydro-1,3,5-triazine, 1,3,5-tris(3,5-dicyclohexyl-4-hydroxybenzyl) isocyanurate.

1.11. Benzylphosrphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzyiphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hdroxyhenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)proDionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethyloipropane, 4-hydroxymethyl-1-phospha-2,6,7-trioxabicyclo[2.2.2]octane.

1.15. Esters of β-(3,5-dicyclohexyl-4-hydroxhenyl) rropionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyf]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)—N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N', N'-tetramethyl-4,4'-diaminodiphenyimethane, 1,2-bis[2-methylphenyl)amino]ethane, 1,2-bis(phenylamino) propane, (o-tolyl)biguanide, bis[4-(1',3'-dimethylbutyl) phenyl]amine, tertoctylated N-phenyl-1-naphthylamine, a mixture of mono- and dialkylated tert-butyl/ tertoctyidiphenylamines, a mixture of mono- and dialkylated nonyidiphenylamines, a mixture of mono- and dialkylated dodecyidiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- and dialkylated tert-butyltert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxy-carbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$-]$_2$ where R=3'-tert-butyl-4'-hydroxy-5'-2H-benzotriazol-2-ylphenyl, 2-[2'-hydroxy-3'-((α,α-dimethylbenzyl)-5'-(1,1,3,3-tetramethylbutyl)-phenyl]benzotriazole; 2-[2'-hydroxy-3'-(1,1,3,3tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyt salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of $^2$-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotfiacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6pentamethylpipefidyl)-

2-n-butyl-2-(2-hydroxy-3,5-di-tertbutylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4.6-bis(4-n-butylamino-2.2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyJ)-2-(4-methoxyphenyl)ethene, N,N'-bisformyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siioxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyll-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]penyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitriloftriethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alphα-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole. zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-12-hydroxyethoxylphenyiabenofuran-2-one], 5,7-di-tert-butyl-3-(4-ethoxyphenyl)benzofuran-2one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyt)-5,7-di-tert-butyl-benzofuran-2-one.

The weight ratio of the product or the mixture according to this invention to the conventional additives may be, for example, 1:0.5 to 1:5.

The products or mixtures of this invention can also be used as stabilizers, especially as light stabilizers, for almost all materials known in the art of photographic reproduction and other reproduction techniques as e.g. described in Research Disclosure 1990, 31429 (pages 474 to 480).

The invention is illustrated in more detail by the following Examples. All parts and percentages are by weight, unless otherwise indicated.

In the structural formulae of the following examples, n' indicates that there are repetitive units in the molecules and the products obtained are not uniform.

The starting material disclosed in the Example 1A is characterized by the number average molecular weight $\overline{M}n$ and the polydispersity $\overline{M}w/\overline{M}n$.

GPC (Gel Permeation Chromatography) is used as an analytical procedure for separating molecules by their difference in size and to obtain molecular weight averages($\overline{M}w$, $\overline{M}n$) or information on the molecular weight distribution of polymers.

The technique is well known and described, for instance, in "Modern Size—Exclusion Liquid Chromatography" by W. W. Yan et al., edited by J. Wiley & Sons, N.Y., USA, 1979, pages 4–8, 249–283 and 315–340.

The GPC analysis shown in the following Examples is carried out with a HPLC instrument, type ®TSP AS-1000, equipped with an ®UV 1000 UV/VIS detector having a wavelenght of 250 nm. A "GPC-SS-250×7.7 mm×⅜" ®Valco-Microgel-3 mixed gel is used as column.

The eluant (flow: 1 ml/min) is tetrahydrofurane-®Uvasol for spectroscopy (®Merck-1.00016)+0.02 mol/L diethanolamine (®Fluka 31590). 0.5 g of the sample to be examined is dissolved in 100 ml of the eluant.

The injection volume is 20 µL and the chromatogram period is 15 min.

EXAMPLE I-1

Preparation of the Product of the Formula

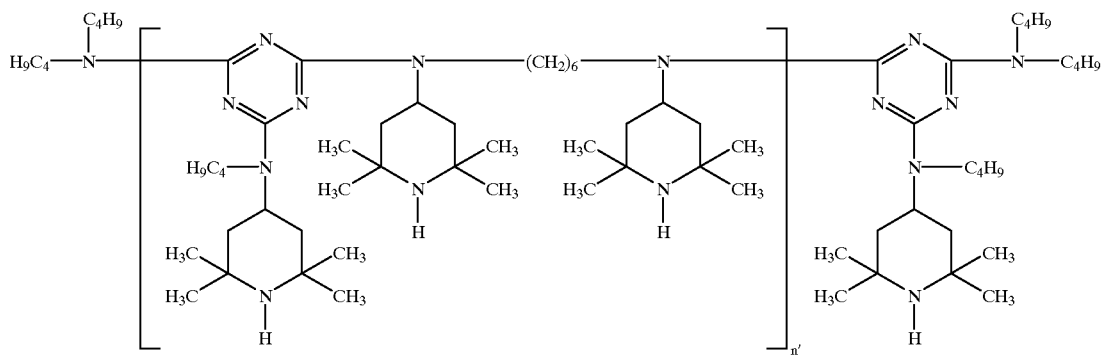

To a solution of 221.2 g (1.2 moles) of cyanuric chloride in 1286 g of xylene, under stirring and nitrogen atmosphere, 254.8 g (1.2 moles) of N-(2,2,6,6-tetramethyl-4-piperidyl)-n-butylamine are added over 3 hours, keeping the temperature of about 30° C. during the addition. A thick but well stirrable suspension is obtained which is kept at the above mentioned temperature for additional 15 minutes. Subsequently, a mixture of 176.3 g of an aqueous solution of NaOH 30% (% w/v) and 200 ml of water is added over 1 hour at about 30° C. The reaction mixture is maintained at about 30° C. for further 2.5 hours. During this time, all solids are dissolved and an emulsion is formed. Then, the aqueous basic solution is separated off.

The remaining xylene solution is heated to 50° C. and 236.8 g (0.6 moles) of N,N'-bis(2,2,6,6-tetramethyl-4-piperidyl)-1,6-hexanediamine in 200 g of water are added over 2 hours. Subsequently, 176.3 g of an aqueous solution of NaOH 30% (% w/v) are added over 2 hours. During the addition, the temperature is maintained at about 50° C. Then, the temperature is increased over 1 hour to about 80° C. The reaction mixture is maintained, under stirring, at 80° C. for further 1.5 hours.

The aqueous basic solution is separated off at about 80° C. and 380 g of xylene are distilled off under vacuum (68–82° C., 200–120 mbar).

To the organic solution, maintained at about 80° C., 118.4 9 (0.3 moles) of N,N'-bis(2,2,6,6-tetramethyl-4-piperidyl)-1,6-hexanediamine are added over 5 minutes. Subsequently, the reaction mixture is stirred for 5 minutes and 92 9 of an aqueous solution of NaOH 30% (% w/v) are added at about 80° C. over 5 minutes. Then, the reaction mixture is transferred to a pressure reactor. 300 g of water and 170 g of xylene are added and, after closing the reactor and inertization with nitrogen, the temperature is raised to 160° C. over 2 hours. The mixture is maintained at 160° C. for 9 hours under 5.4 bar of pressure.

After cooling to 60° C., 89.0 g (0.69 moles) of di-nbutylamine are added over 5 minutes and subsequently, 86.4 g of an aqueous solution of NaOH 30% (% w/v) are added over 5 minutes.

After closing the reactor again, the mixture is heated to 160° C. over 1 hour and maintained at 160° C. for 4 hours under 5 bar of pressure.

After cooling to 600°, 130 g of xylene and 150 g of water are added. The mixture is heated to 90° C. under stirring. The aqueous solution is separated off.

The organic phase is washed twice with 400 g of water and azeotropically dried. The solution is cooled to about 30° C., filtered and concentrated under vacuum (125–230° C./350–1 mbar). Upon cooling, the melt product gives a solid.

The melting point of the product obtained is 133–137° C.

$\overline{Mn}$ (by GPC=gel permeation chromatography)=2200 g/mol $\overline{Mw}/\overline{Mn}$=1.6

The GPC analysis shows a chromatogram as in FIG. 1. Analysis of the Product Obtained:

Compound with n'=1: 39 mol %
Compound with n'=3: 20 mol %
Compound with n'=5: 9.3 mol %
Compound with n'=7: 4.4 mol %

EXAMPLE 1–2

Preparation of the Product of the Formula 63.7 g (0.3 moles) of N-(2,2,6,6-tetramethyl-4-piperidinyl)-n-butylamine are added, keeping the temperature of about 5° C. during the addition.

Then, 40 ml of water are added together with an aqueous solution of NaOH 30% (% w/v).

After the addition, the mixture is heated to room temperature and 59.2 9 (0.15 moles) of N,N'-bis(2,2,6,6-tetramethyl-4-piperidinyl)-1,6-hexanediamine in 125 ml of methyl isobutyl ketone are added at room temperature.

The mixture is then heated to 60° C. and, after a further addition of 40 ml of water, maintained at 60° C. for 1 hour.

40 g of an aqueous solution of NaOH 30% (% w/v) are added and the mixture is heated to 70° C. After ½ hour, 200 ml of methyl isobutyl ketone and 30 ml of water are distilled off at 70° C. under a light vacuum.

To the organic mixture kept at 70° C., 29.6 g (0.075 moles) of N,N'-(2,2,6,6-tetramethyl-4-piperidinyl)-1,6-hexanediamine are added and further 20 g of an aqueous solution of NaOH 30% (% w/v) are added.

Then, the reaction mixture is transferred to a pressure reactor. 50 ml of methyl isobutyl ketone and 40 ml of water are added and, after closing the reactor and inertization with nitrogen, the temperature is raised to 160° C.

The mixture is maintained at 160° C. for 4 hours under 6 bar of pressure.

After cooling to 60° C., 36.6 g (0.17 moles) of N-(2,2,6,6-tetramethyl-4-piperidinyl)-n-butylamine are added together with 20 g of an aqueous solution of NaOH 30% (% w/v).

After closing the reactor again, the mixture is heated to 140° C. and maintained at 140° C. for 4 hours under 5 bar of pressure.

After cooling to 50° C., 125 ml of methyl isobutyl ketone and 100 ml of water are added.

The aqueous basic solution is separated off and the organic phase is washed once with 100 ml of water.

The organic phase is concentrated under vacuum at 220° C./20 mbar.

After cooling, the melt product gives a solid with m.p.=172–174° C.

$\overline{Mn}$ (by GPC)=2080 g/mol $\overline{Mw}/\overline{Mn}$=1.52

The GPC analysis shows a chromatogram as in FIG. 2. Analysis of the Product Obtained:

Compound with n'=1: 31 mol %
Compound with n'=3: 23 mol %

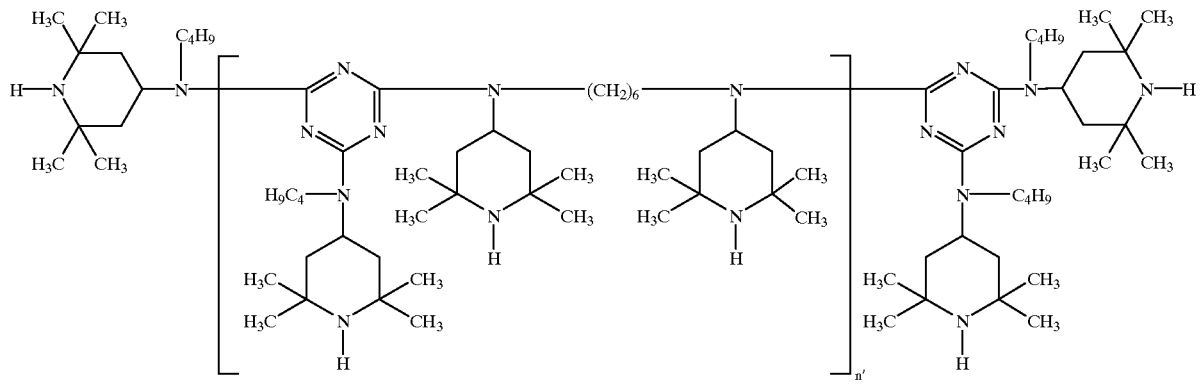

To a solution of 55.3 g (0.3 moles) of cyanuric chloride in 250 ml of methyl isobutyl ketone, maintained at about 5° C., Compound with n'=5: 5 mol %
Compound with n'=7: 1 mol %

EXAMPLE 1

Preparation of the Product of the Formula

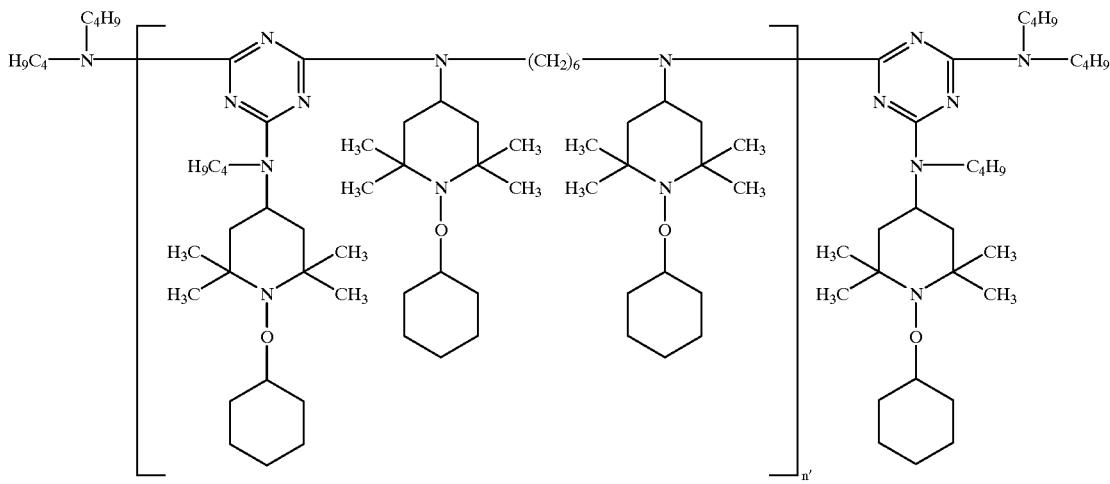

A mechanically stirred 1.0 L 4 neck flask is charged with 40.0 g (0.16 moles) of the product according to I-1, 0.40 g of $MoO_3$ and 320 ml of cyclohexane. The mixture is heated to reflux. 82.4 g (0.64 moles) of 70% t-butylhydroperoxide are added within 30 minutes. Water is collected by azeotropic distillation and reflux is continued for one hour. The reaction mixture is transferred to a magnetically stirred glass pressure bottle and heated at 130° C. for 5 hours. The reaction mixture is cooled to 70° C. and $MoO_3$ is filtered off. The filtrate is washed with a solution of 20 g of $Na_2SO_3$ in 100 ml of $H_2O$ for one hour at 60° C. The phases are separated, the organic phase is dried over $MgSO_4$ and the total volume is reduced to 100 ml. The solution is drowned in 500 ml of methanol at 5° C. The precipitate is filtered and dried to 52.8 g (95% of theory). The product obtained has a melting range of 140°–170° C.

$^1$H NMR: 0.85–2.40 ppm (complex mixture); 3.25–3.35 ppm (s, broad, $NCH_2$); 3.62 ppm (s, broad, NOCH); 4.90–5.40 ppm (broad, NCH).

$^{13}$C NMR: 81.8 ppm (NOCH); 165 ppm (triazine C).

The ratio of protons at 3.25, 3.62 and 4.90 ppm is 2:1:1.

EXAMPLE 1-A

Preparation of the Product of the Formula

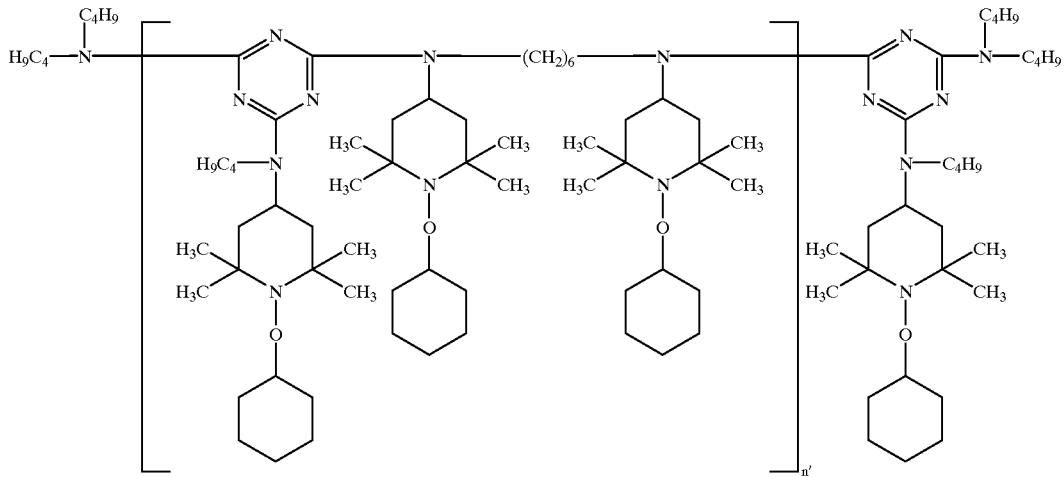

A mixture of 885 g (3.54 moles) of the product of Example I-1, 6000 g (71.4 moles) of cyclohexane and 2.2 g of molybdenum trioxide is heated to reflux. A solution of 3360 g of 70% aqueous t-butyl hydroperoxide (26.1 moles) is added to the refluxing mixture over 1–2 hours and water is removed by azeotropic distillation. The reaction mass is transferred to a pressure reactor and heated at 125° C. at 30–50 psig (2.1–3.5 bar) until the red color is discharged. The crude reaction mass is cooled and treated with aqueous sodium sulfite to destroy residual peroxide. The aqueous layer is split off and the organic layer is concentrated under reduced pressure to a melt which is fed slowly into cold methanol to obtain, after filtration, an off white solid product.

Average transmission values (10% toluene): 425 nm=21.8%; 450 nm=37.4%; 475 nm=62.6%

EXAMPLE 1-B

Preparation of the Product of the Formula

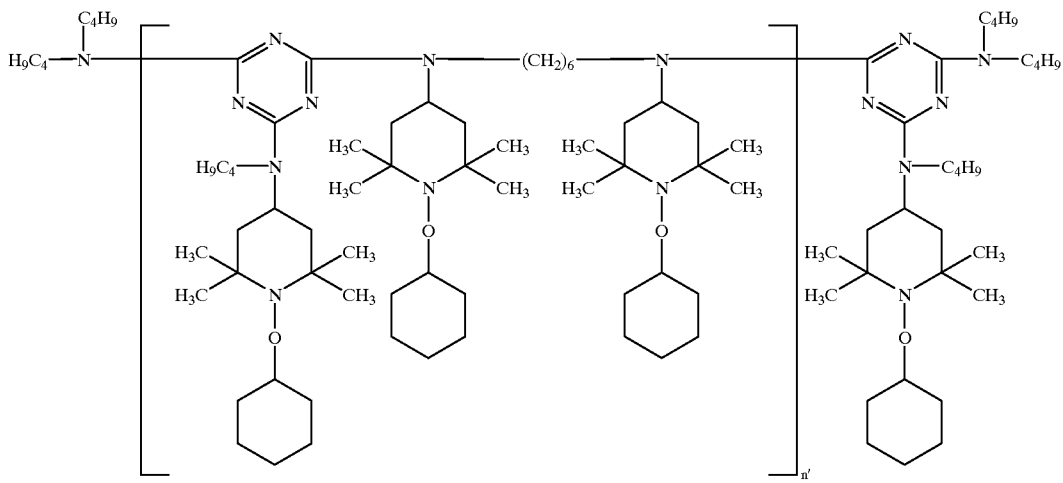

The procedure of Example 1-A is repeated, except that during work-up, the melt obtained after cyclohexane is removed is diluted with t-butyl alcohol and concentrated to 50% solids. The solution is cooled and cold methanol is rapidly added to afford, after filtration, an off white solid product.

Average transmission values (10% toluene): 425 nm=57.0%; 450 nm=71.5%; 475 nm=79.7%

EXAMPLE 2

Preparation of the Product of the Formula

A mechanically stirred 1.0 L 4 necked round bottom flask is charged with 40.0 g (0.160 moles) of the product according to Example I-1, 0.40 9 of $MoO_3$ and 320 ml of n-octane. The mixture is heated to reflux and 82.4 g (0.640 moles) of t-butylhydroperoxide are added within 30 minutes. Water is separated by azeotropic distillation and reflux is continued for 90 minutes. The reaction mixture is transferred to a magnetically stirred pressure bottle and heated at 135° C. for 3 hours. $MoO_3$ is filtered and the filtrate is washed with a solution of 20 g of $Na_2SO_3$ in 100 ml of $H_2O$ for 30 minutes at 60° C. The phases are separated, the organic phase is washed with 100 ml of water and then with 100 ml of saturated NaCl. The organic phase is dried over $MgSO_4$ and then evaporated to 100 ml total volume. The solution is drowned in 500 ml of methanol at 5° C. The precipitate, a soft glass, is dried for 1 hour in a vacuum oven of 55° C. The product, now a hard glass, is crushed with a mortar and then dried to 47.4 g (78% of theory). The product has a melting range of 95–120° C.

$^1$H NMR: 0.82–2.40 ppm (complex mixture); 3.25–3.40 ppm (s, broad, $NCH_2$); 3.60–3.92 ppm (complex, NOCH and $NCH_2$ of $NC_4H_9$); 4.90–5.40 ppm (complex, NCH).

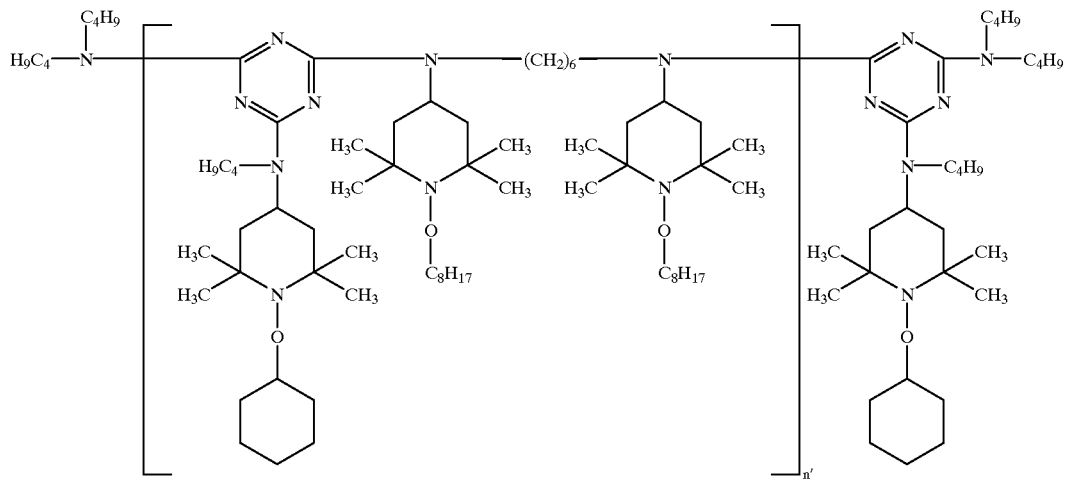

$^{13}$C NMR: 78.6–83.4 ppm (three peaks, NOCH); 165 ppm (triazine C).

The ratio of protons at 3.25 and 4.90 is 2:1.

EXAMPLE 2-A

Preparation of the Product of the Formula

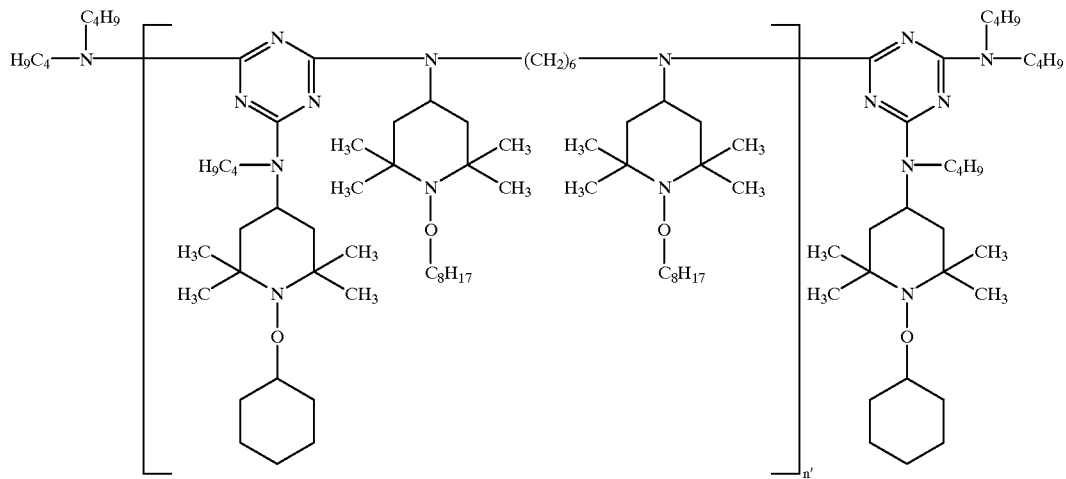

A mixture of 1304 g (5.21 moles) of the product of Example I-1, 10.3 kg (90.2 moles) of octane and 4.0 g of molybdenum trioxide is heated to reflux. A solution of 3873 g of 70% aqueous t-butyl hydroperoxide (30.1 moles) is added to the refluxing mixture over 1–2 hours and water is removed by azeotropic distillation. The reaction mass is heated at reflux at atmospheric pressure until the red color is discharged. The crude reaction mass is cooled and treated with aqueous sodium sulfite to destroy residual peroxide. The aqueous layer is split off and the organic layer is concentrated under reduced pressure to a melt which is fed slowly into cold methanol to obtain, after filtration, an off white solid product.

Average transmission values (10% xylene): 425 nm=39.3%; 450 nm=75.1%; 475 nm=87.3%

EXAMPLE 2-B

Preparation of the Product of the Formula

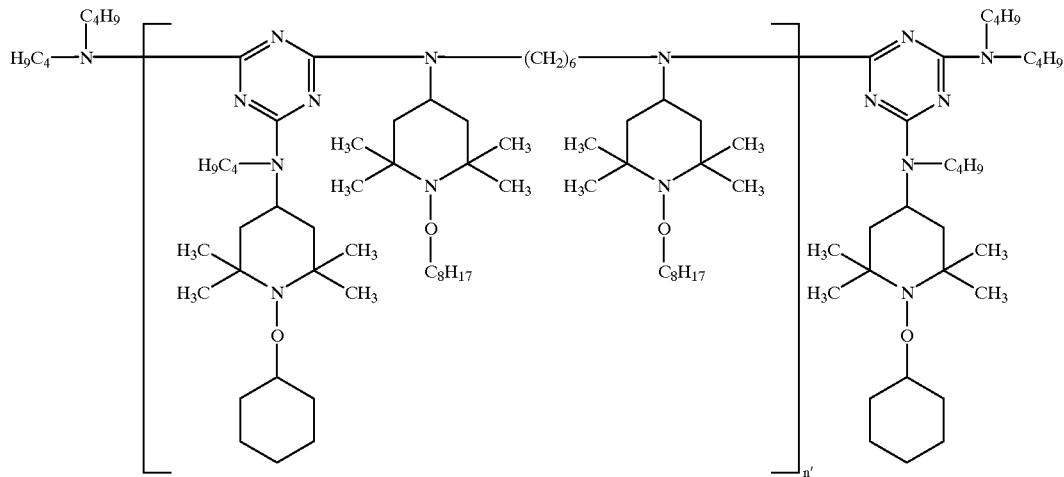

The procedure of Example 2-A is repeated, except that during work-up, the melt obtained after octane is removed is diluted with tbutyl alcohol and concentrated to 50% solids. The solution is cooled and cold methanol is rapidly added to afford, after filtration, an off white solid product.

Average transmission values (10% toluene): 425 nm=59.8%; 450 nm=82.5%; 475 nm=91.2%

EXAMPLE 1-A

Light-stabilizing Action in Polypropylene Fibres.

2.5 g of the stabilizer shown in Table 1, 1 g of tris(2,4-di-t-butylphenyl) phosphite, 1 g of calcium monoethyl 3,5-di-t-butyl-4-hydroxybenzyl-phosphonate, 1 g of calcium stearate and 2.5 g of titanium dioxide are mixed in a slow mixer with 1000 g of polypropylene powder having a melt index=12 g/10 min (measured at 230° C. and 2.16 kg).

The mixtures are extruded at 200–230° C. to obtain polymer granules which are then converted into fibres using a pilot-type apparatus (®Leonard-Sumirago(VA), Italy) and operating under the following conditions:

| | |
|---|---|
| Extruder temperature: | 230–245° C. |
| Head temperature: | 255–260° C. |
| Draw ratio: | 1:3.5 |
| Linear density: | 11 dtex per filament |

The fibres prepared in this way are exposed, after mounting on white cardboard, in a 65 WR Weather-O-Meter (ASTM D2565-85) with a black panel temperature of 63° C.

For samples taken after various times of exposure to the light, the residual tenacity is measured using a constant-speed tensometer, and the exposure time in hours needed to halve the initial tenacity ($T_{50}$) is then calculated.

TABLE 1

| Stabilizer | $T_{50}$ in hours |
|---|---|
| Compound of Example I-1 | 3490 |

The compound listed in Table 1 shows a good light-stabilizing activity in polypropylene fibres.

EXAMPLE 1-B

Pigment Interaction in Polypropylene Plaques 5.625 g of the stabilizer shown in Table 2, 13.500 g of Pigment Blue 15 "Flush" (50% mixture in polyethylene) and 25.875 g of polypropylene powder (having a melt index of approximately 14 measured at 230° C. and 2.16 Kg) are added to fill a ®Haake internal mixer at room temperature (®Haake Buchler Rheochord System 40 using a 60 cc 3 piece Rheomixer with cam blades). The cam blades are rotating at 5 RPM (revolutions per minute). A ram closed the bowl under a weight of 5 kg. The temperature is increased to 180° C. and held at 180° C. The total time is 30 minutes.

The mixture is removed while at 180° C. after 30 minutes and cooled down to room temperature. The mixture so obtained—called the "concentrate"—will be used again.

0.900 g of this concentrate, 3.600 g of titanium dioxide "Flush" (50% mixture in polyethylene), and 40.500 g of polypropylene powder (having a melt index of approximately 14 measured at 230° C. and 2.16 Kg) are added to a ®HAAKE mixer bowl at 160° C. The cam blades are rotating at 20 RPM. A ram closes the bowl under a weight of 5 kg. The temperature is increased to 170° C. and the RPM is increased to 125. The total time is 30 minutes.

The molten mixture is removed at 170° C., transferred to a hand held tool at room temperature and transformed into a round plaque 1 mm×25 mm in diameter. The mixture now so obtained is called the "letdown" and the plaque the "letdown plaque."

Color difference, delta E (CIE color difference equation), of sample letdown plaque containing the stabilizer indicated in Table 2 versus control letdown plaque without the stabilizer are measured. The measurement is done using an Applied Color Systems Spectrophotometer Model CS-5 (USA). The measurement parameters used are 400–700 nm—scan, small area view, reflectance, illuminate D65, 10 degree observer.

The above processing conditions are designed to simulate the manufacture of concentrates (masterbatches) of pigments and stabilizers and the subsequent let-down (dilution) into finished plastic articles.

A high delta E indicates pigment agglomeration and poor dispersion. A delta E of 0.5 or less will not be seen as different by the eye.

TABLE 2

| Stabilizer | Delta E |
|---|---|
| Compound of Example I-1 | 0.5 |

The stabilizer listed in Table 2 shows low pigment interaction in polypropylene plaques. This is advantageous.

EXAMPLE 1-C

Light-stabilizing Action in Polypropylene Tapes.

1 g of each of the compounds listed in Table 3, 1 g of tris[2,4-di-tert-butylphenyl] phosphite, 0.5 g of pentaerythritol tetrakis[3-(3,5-di-tert-butyl-4-hydroxyphenyl) propionate] and 1 g of calcium stearate are mixed in a turbomixer with 1000 g of polypropylene powder having a melt index of 2.1 (measured at 230° C. and 2.16 Kg).

The mixtures are extruded at 200–220° C. to give polymer granules which are subsequently converted to stretched tapes of 50 μm thickness and 2.5 mm width, using a semi-industrial type of apparatus (®Leonard-Sumirago (VA)—Italy) and working under the following conditions:

| | |
|---|---|
| Extruder temperature: | 210–230° C. |
| Head temperature: | 240–260° C. |
| Stretch ratio: | 1:6 |

The tapes thus prepared are mounted on a white card and exposed in a Weather-O-Meter 65 WR (ASTM D 2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

TABLE 3

| Stabilizer | $T_{50}$ in hours |
|---|---|
| Compound of Example I-1 | 3170 |

The compound listed in Table 3 shows a good light-stabilizing activity in polypropylene tapes.

EXAMPLE 1-D

Antioxidant Action in Polypropylene Plaques.

1 g of each of the compounds listed in Table 4 and 1 g of calcium stearate are mixed in a slow mixer with 1000 g of polypropylene powder having a melt index of 4.3 (measured at 230° C. and 2.16 Kg).

The mixtures are extruded at 200–220° C. to give polymer granules which are then converted into plaques of 1 mm thickness by injection-moulding at 220° C.

The plaques are then punched using a DIN 53451 mould and the specimens obtained are exposed in a forced circulation air oven maintained at a temperature of 1 35° C.

The specimens are checked at regular intervals by folding them by 180° in order to determine the time (in hours) required for fracturing them.

TABLE 4

| Stabilizer | Time in hours required for fracturing |
| --- | --- |
| Compound of Example I-1 | 1830 |

The compound listed in Table 4 is a good antioxidant in polypropylene plaques.

EXAMPLE 1-E

Color of Polypropylene Plaques after Oven Ageing 5 g of each of the compounds listed in Table 5, 1 g of tris[2,4-di-tert-butylphenyl] phosphite, 1 g of pentaerythritol tetrakis[3-(3,5-di-tert-butyl-4-hydroxyphenyl) propionate] and 1 g of calcium stearate are mixed in a slow mixer with 1000 g of polypropylene powder having a melt index of 2.1 (measured at 230° C. and 2.16 Kg).

The mixtures are extruded twice at 200–220° C. to give polymer granules which are then converted into plaques of 1 mm thickness by compression-moulding at 230° C. for 6 minutes.

The plaques are then exposed for seven days in a forced circulation air oven maintained at 120° C. After the oven exposure, the Yellowness Index (YI) of the plaques is measured according to ASTM D 1925 by ®MINOLTA CR 210 chromometer (MINOLTA—Japan).

TABLE 5

| Stabilizer | YI according to ASTM D 1925 |
| --- | --- |
| Compound of Example I-1 | 18.7 |

The polypropylene plaques stabilized with the compound listed in Table 5 have a good Yellowness Index after oven ageing.

EXAMPLE 1-F

Rotational Molding

Linear low density polyethylene (Hexene-Copolymer, ®Quantum MP635–661; Ml=6.5 dg/min; density=0.935 g/cm$^3$), containing 0.05% of zinc stearate, 0.05% of pentaerythritol tetrakis[3-(3,5-di-tert-butyl-4-hydroxyphenyl) propionate] and 0.10% of tris[2,4-di-tert-butylphenyl] phosphite, is dry blended with 0.17% of the compound of Example I-1 and then melt compounded at 234° C. into pellets. The pelletized fully formulated resin is ground into a powder using a Reduction Engineering Model 50 Pulverizer (particle size between 100 mesh and 35 mesh). The ground resin is placed in a cast aluminum mold (16"×16"× 6") which is rotated biaxially in a gas fired oven in a laboratory scale rotational molder (FSP M20 ®Clamshell). Processing conditions are either: 15 min at 288° C. (=Condition 1) or 12 min at 316° C. (=Condition 2).

a) Color Determination

The molded boxes are cut into 2"×2" plaques and exposed in a Blue M forced draft oven at 120° C. Yellowness index is determined on an Applied Color Systems spectrophotometer by reflectance mode according to ASTM D 1925.

The samples containing the compound of Example I-1 exhibit low color after molding and after thermal aging.

b) UV Light-stabilizing Activity

Other 2"×2" plaques cut from the molded boxes are exposed in an ®Atlas Xenon-Arc-Weather-O-Meter according to ASTM G26 at 63° C. pbt, 0.35 kW/cm$^2$ at 340 nm. Samples are tested periodically for change in impact strength using a ®Dynatup Model 8250 Drop Tower. Failure in this test is determined by the observation of the loss of impact strength of the plaques. The longer it takes for this loss in properties to occur, the more effective is the stabilizer system.

The plaques containing the compound of Example I-1 exhibit good light-stabilizing activity as determined by the above criteria.

EXAMPLE A

Pigmented thermoplastic olefin (TPO) pellets are prepared by mixing a polyolefin blend (polypropylene containing an ethylene-propylene copolymer; ®Polytrope TPP 518-01 from ®A. Schulman, Inc.; Akron, Ohio, USA) with the additives listed below in a ®Superior/MPM 1" single screw extruder with a general all-purpose screw (24:1 L/D) at 200° C., cooling in a water bath and pelletizing. Prior to extrusion and molding, the additives are dry blended in a tumble dryer.

Additives:

0.25%[*)] of ®Red 3B (Pigment Red 177, Color Index 65300), 0.2%[*)] of 2-(2'-hydroxy-3',5'-di-tert-amylphenyl) benztriazol, 0.2%[*)] of bis(1-octyloxy-2,2,6,6-tetramethyl-4-piperidyl) sebacate, 0.1%[*)] of calcium stearate, about 10%[*)] of talc and The Stabilizers Listed in Table 6

[*)] weight percent based on the polyolefin blend

The resulting pellets are molded into 1.524 mm thick 2"×2" plaques at about 190° C. on a ®BOY 30M Injection Molding Machine.

The test plaques are mounted in metal frames and exposed in an ®Atlas Ci65 Xenon Arc Weather-O-Meter at 70° C. black panel temperature, 0.55 W/m$^2$ at 340 nanometers and 50% relative humidity with intermittent light/dark cycles and water spray (®Society of Automotive Engineers—SAE J 1960 Test Procedure—Exterior Automotive conditions).

Gloss measurements of the test specimens are conducted on a ®BYK-GARDNER Haze/Gloss Meter at 60° according to ASTM D 523.

The results are shown in Table 6.

TABLE 6

| Stabilizers | Gloss Retention after hours Weather-O-Meter | |
|---|---|---|
| | 0 hours ($\hat{=}$ 0 kJ/m$^{2**}$) | 1890 hours ($\hat{=}$ 2500 kJ/m$^{2**}$) |
| 0.05%*) of pentaerythritol tetrakis[3-(3,5-di-tert-butyl-4-hydroxyphenyl)propionate], 0.05%*) of tris[2,4-di-tert-butylphenyl]phosphite, 0.20%*) of the compound of Example 1 | 100.0% | 90.5% |
| 0.05%*) of pentaerythritol tetrakis[3-(3,5-di-tert-butyl-4-hydroxyphenyl)propionate,] 0.05%*) of tris[2,4-di-tert-butylphenyl]phosphite, 0.20%*) of the compound of Example 2 | 100.0% | 91.9% |
| 0.05%*) of di(hydrogenated tallow)-hydroxylamine 0.20%*) of the compound of Example 1 | 100.0% | 87.3% |
| 0.05%*) of di(hydrogenated tallow)-hydroxylamine 0.20%*) of the compound of Example 2 | 100.0% | 88.0% |

*)weight percent based on the polyolefin blend
**)refers to incident energy expressed as kJ/m$^2$ measured at 340 nm The formulations containing the stabilizers listed in Table 6 show much greater resistance to photodegradation than those without said stabilizers. The unstabilized test specimens fail quickly under the UV exposure outlined above.

EXAMPLE B

Fiber grade polypropylene containing 0.05% by weight of calcium stearate and 0.05% by weight of di(hydrogenated tallow) hydroxylamine as base stabilization is dry blended with the stabilizer indicated in Table 7 and then melt compounded at 234° C. into pellets. The pelletized fully formulated resin is then spun at 246° C. or 274° C. into fiber using a ®Hills laboratory model fiber extruder. The spun tow of 41 filaments is stretched at a ratio of 1:3.2 to give a final denier of 615/41.

"Socks" are knitted from the stabilized polypropylene on a ®Lawson-Hemphill Analysis Knitter and exposed in an ®Atlas Xenon-Arc-Weather-Ometer using SAE J1 885 Interior Automotive conditions at 89° C. bpt, 0.55 kW/cm$^2$ at 340 nm with no spray cycle. Failure in this test is determined by the observation of the physical failure of the sock when it is "scratched" with a blunt glass rod. The longer it takes for this catastrophic failure to occur, the more effective is the stabilizer.

The results are shown in Table 7.

TABLE 7

| Stabilizer | Catastrophic Failure Time Fiber Spun at 246° C. | Catastrophic Failure Time Fiber Spun at 274° C. |
|---|---|---|
| None | 192 hours | 96 hours |
| 0.25% by weight of the compound of Example 1 | 600 hours | 408 hours |
| 0.25% by weight of the compound of Example 2 | 600 hours | 408 hours |

What is claimed is:

1. A product obtained by 1) reacting a compound of the formula (a)

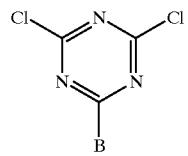

(a)

with a compound of the formula (b)

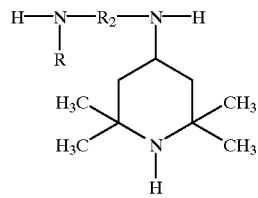

(b)

in a stoichiometric ratio to obtain a compound of the formula (g);

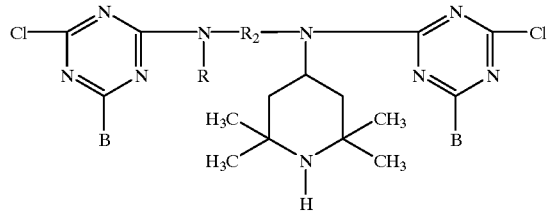

(g)

2) reacting the compound of the formula (b) with the compound of the formula (g) in a molar ratio of 0.4:1 to 0.75:1;

3) reacting the end groups of the formula (d)

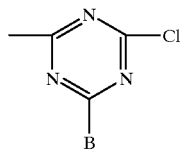

(d)

being present in the product of the reaction 2) with a compound of the formula (e)

A—H  (e)

in a molar ratio of 2:1.7 to 2:3;

the reactions 1) to 3) being carried out in an organic solvent in the presence of an inorganic base; and 4) transferring the groups of the formula (G-I)

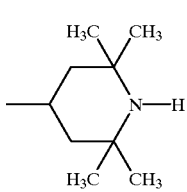
(G-I)

being present in the product of the reaction 3) to groups of the formula (G-II);

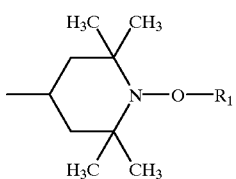
(G-II)

said transfer being carried out by reacting the product of the reaction 3) with a hydroperoxide in a hydrocarbon solvent in the presence of a peroxide decomposing catalyst;

$R_1$ is a hydrocarbyl radical or —O—$R_1$ is oxyl;

$R_2$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (I-a), (I-b) or (I-c);

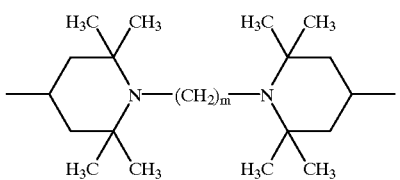
(I-a)

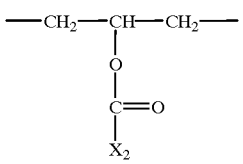
(I-b)

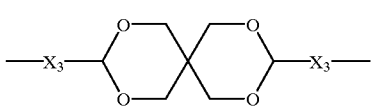
(I-c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

A is —$OR_3$, —$N(R_4)(R_5)$ or a group of the formula (II);

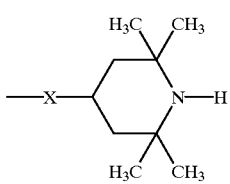
(II)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

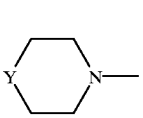
(III)

with Y being —O—, —$CH_2$—, —$CH_2CH_2$— or >N—$CH_3$;

and $R_3$ is additionally hydrogen or —$N(R_4)(R_5)$ is additionally a group of the formula (III);

X is —O— or >N—$R_6$;

$R_6$ is $C_1$–$C_{18}$alkyl, $C_3$–$C_{18}$alkenyl, $C_5$–$C_{12}$cycloalkyl which is unsubstituted or substituted by 1, 2 or $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-I), or $C_2$–$C_4$alkyl which is substituted in the 2, 3 or 4 position by —OH, $C_1$–$C_8$alkoxy, di($C_1$–$C_4$alkyl)amino or a group of the formula (III);

R has one of the meanings given for $R_6$; and

B has one of the meanings given for A.

2. A product according to claim 1 wherein $R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—$X_1$ with $X_1$ being $C_1$–$C_{12}$acyl or ($C_1$–$C_{12}$alkoxy)carbonyl or having one of the definitions of $R_4$; or $R_2$ is a group of the formula (I-b);

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl;

and $R_3$ is additionally hydrogen or —$N(R_4)(R_5)$ is additionally a group of the formula (III);

$R_6$ is $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (G-I).

3. A product according to claim 1 wherein R is a group of the formula (G-I).

4. A product according to claim 1 wherein $R_2$ is $C_2$–$C_{10}$alkylene, cyclohexylene, cyclohexylenedi($C_1$–$C_4$alkylene), $C_1$–$C_4$alkylene-dicyclohexylene or phenylenedi($C_1$–$C_4$alkylene);

$R_3$, $R_4$ and $R_5$, which are identical or different, are $C_1$–$C_{12}$alkyl, $C_5$–$C_7$cycloalkyl which is unsubstituted or substituted by 1, 2 or 3 $C_1$–$C_4$alkyl; phenyl which is unsubstituted or substituted by 1, 2 or 3 $C_1$–$C_4$alkyl; benzyl which is unsubstituted or substituted on the phenyl by $C_1$–$C_4$alkyl; or —N($R_4$)($R_5$) is additionally a group of the formula (III); and $R_6$ is $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; or a group of the formula (G-I).

5. A product according to claim 1 wherein $R_2$ is $C_2$–$C_8$alkylene;

$R_3$, $R_4$ and $R_5$, which are identical or different, are $C_1$–$C_8$alkyl, cyclohexyl which is unsubstituted or substituted by methyl; phenyl which is unsubstituted or substituted by methyl; benzyl or —N($R_4$)($R_5$) is additionally 4-morpholinyl; and $R_6$ is $C_1$–$C_8$alkyl, cyclohexyl which is unsubstituted or substituted by methyl; benzyl or a group of the formula (G-I).

6. A product according to claim 1 wherein $R_1$ is octyl or cyclohexyl, and the hydrocarbon solvent in the reaction 4) is, octane or cyclohexane;

$R_2$ is $C_2$–$C_6$alkylene;

A is —N($R_4$)($R_5$) or a group of the formula (II);

$R_4$ and $R_5$, which are identical or different, are $C_1$–$C_8$alkyl;

or —N($R_4$)($R_5$) is additionally 4-morpholinyl;

X is >$NR_6$;

$R_6$ is $C_1$–$C_8$alkyl; and

B has one of the meanings given for A.

7. A product according to claim 1 wherein $R_1$ is octyl or cyclohexyl, and the hydrocarbon solvent in the reaction 4) is, octane or cyclohexane;

$R_2$ is $C_2$–$C_6$alkylene;

R is a group of the formula (G-I);

A is —N($R_4$)($R_5$);

$R_4$ and $R_5$, which are identical or different, are $C_1$–$C_8$alkyl;

B is a group of the formula (II);

X is >$NR_6$;

$R_6$ is $C_1$–$C_8$alkyl.

8. A product according to claim 1 wherein the organic solvent in the reactions 1) to 3) is an aromatic hydrocarbon or an aliphatic ketone and the inorganic base is sodium hydroxide, potassium hydroxide, sodium carbonate or potassium carbonate.

9. A product according to claim 1 wherein the reaction 1) is carried out at a temperature of 10° to 90° C., the reaction 2) is carried out at a temperature of 110° to 200° C. and the reaction 3) is carried out at a temperature of 110° to 180° C.

10. A product according to claim 1 wherein the reactions 2) and 3) are carried out under pressure.

11. A product according to claim 1 wherein $R_1$ is $C_5$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent in the reaction 4) is $C_5$–$C_{18}$alkane, $C_5$–$C_{18}$alkene, $C_5$–$C_{18}$alkyne, $C_5$–$C_{12}$cycloalkane unsubstituted or substituted by $C_1$–$C_4$alkyl; $C_5$–$C_{12}$cycloalkene unsubstituted or substituted by $C_1$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

12. A product according to claim 1 wherein $R_1$ is heptyl, octyl, cyclohexyl, methylcyclohexyl, cyclooctyl, cyclohexenyl, α-methylbenzyl or 1,2,3,4-tetrahydronaphthenyl, and the hydrocarbon solvent in the reaction 4) is, heptane, octane, cyclohexane, methylcyctohexane, cyclooctane, cyclohexene, ethylbenzene or tetralin.

13. A product according to claim 1 wherein $R_1$ is octyl or cyclohexyl, and the hydrocarbon solvent in the reaction 4) is octane or cyclohexane.

14. A product according to claim 1 wherein the radical —O—$R_1$ is oxyl and the hydrocarbon solvent in the reaction 4) is an inert organic solvent.

15. A product according to claim 1 wherein the peroxide decomposing catalyst is a metal carbonyl, metal oxide, metal acetylacetonate or a metal alkoxide where the metal is selected from the groups IVb, Vb, VIb, VIIb and VIII of the periodic table.

16. A product according to claim 1 wherein the hydroperoxide is t-butyl hydroperoxide and the peroxide decomposing catalyst is $MoO_3$.

17. A product according to claim 1 wherein per mole of the group of the formula (G-I)

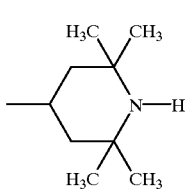

(G-I)

being present in the product of the reaction 3) 2 to 8 moles of the hydroperoxide, 0.001 to 0.1 mole of the peroxide decomposing catalyst and 5 to 30 moles of the hydrocarbon solvent are applied.

18. A product obtained by hydrogenating a product according to claim 1 wherein —$OR_1$ in the formula (G-II) is oxyl to get a corresponding product with groups of the formula (G-III).

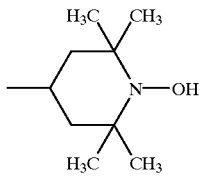

(G-III)

19. A mixture containing a monodispers compound of the formula (P-I), a monodispers compound of the formula (P-II) and a monodispers compound of the formula (P-III), said compounds differing only in the number of the repetitive units,

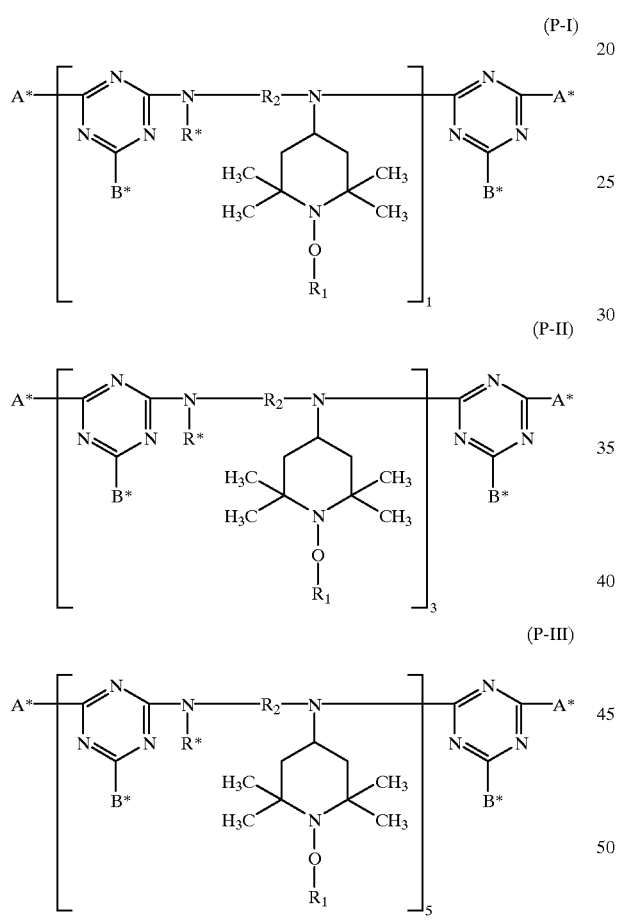

the total amount of the compound of the formula (P-I) being 15 to 45 mol %, the total amount of the compound of the formula (P-II) being 15 to 35 mol % and the total amount of the compound of the formula (P-III) being 3 to 18 mol %, relative to the total mixture; and $R_1$ is hydrogen, a hydrocarbyl radical or —O—R, is oxyl;
$R_2$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (I-a), (I-b) or (I-c);

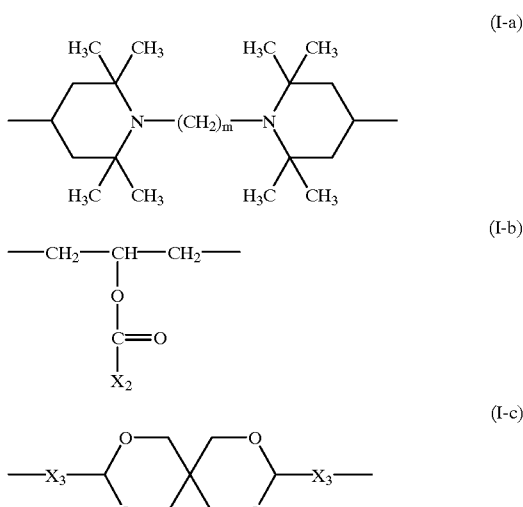

with m being 2 or 3,
$X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and
the radicals $X_3$ being independently of one another $C_2$–$C_{12}$alkylene;
A* is —$OR_3$, —$N(R_4)(R_5)$ or a group of the formula (G-IV));

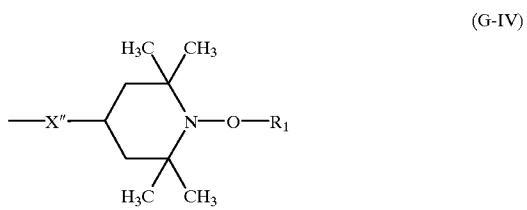

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

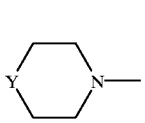

with Y being —O—, —$CH_2$—, —$CH_2CH_2$— or >N—$CH_3$;
and $R_3$ is additionally hydrogen or —$N(R_4)(R_5)$ is additionally a group of the formula (III);
X* is —O— or >N—$R_6$*;

$R_6^*$ is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-II),

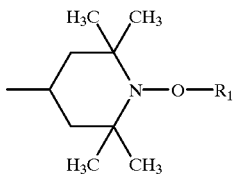

(G-II)

or $C_2$–$C_4$alkyl which is substituted in the 2, 3 or 4 position by —OH, $C_1$–$C_8$alkoxy, di($C_1$–$C_4$alkyl)amino or a group of the formula (III);

R* has one of the meanings given for $R_6^*$; and

B* has one of the meanings given for A*.

20. A mixture according to claim 19 which additionally contains a monodispers compound of the formula (P-IV),

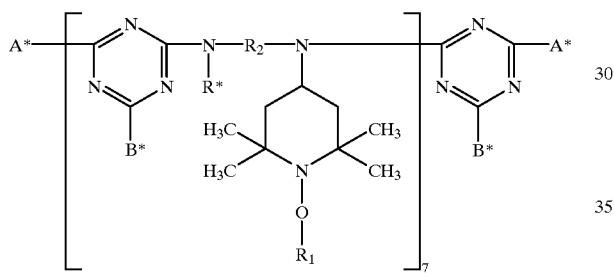

(P-IV)

the total amount of the compound of the formula (P-IV) being 1 to 15 mol %, relative to the total mixture.

21. A composition containing an organic material susceptible to degradation induced by light, heat or oxidation and a product according to claim 1.

22. A composition according to claim 21 wherein the organic material is a synthetic polymer.

23. A composition according to claim 21 wherein the organic material is polyethylene or polypropylene.

24. A method for stabilizing an organic material against degradation induced by light, heat of oxidation, which comprises incorporating into said organic material a product according to claim 1.

25. A product obtained by 1) reacting a compound of the formula (a)

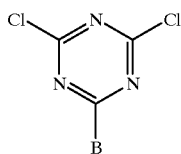

(a)

with a compound of the formula (b-1)

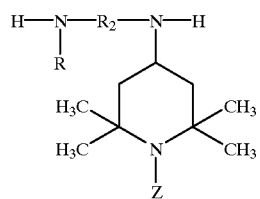

(b-1)

in a stoichiometric ratio to obtain a compound of the formula (g-1);

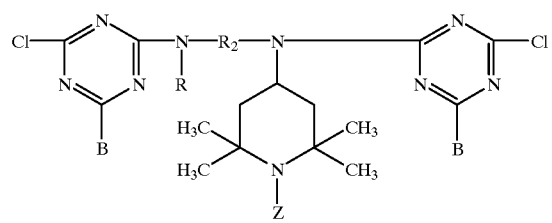

(g-1)

2) reacting the compound of the formula (b-1) with the compound of the formula (g-1) in a molar ratio of 0.4:1 to 0.75:1;

3) reacting the end groups of the formula (d)

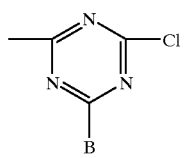

(d)

being present in the product of the reaction 2) with a compound of the formula (e)

A—H  (e)

in a molar ratio of 2:1.7 to 2:3;

the reactions 1) to 3) being carried out in an organic solvent in the presence of an inorganic base;

Z is hydrogen, $C_1$–$C_8$alkyl, $C_2$–$C_8$hydroxyalkyl, O, —OH, $C_1$–$C_{18}$hydrocarbyloxy, —$CH_2CN$, $C_3$–$C_6$alkenyl, $C_3$–$C_6$alkynyl, $C_7$–$C_9$phenylalkyl which is unsubstituted or substituted on the phenyl by 1, 2 or 3 $C_1$–$C_4$alkyl; or $C_1$–$C_8$acyl;

$R_2$ is $C_2$–$C_{12}$alkylene, $C_4$–$C_{12}$alkenylene, $C_1$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below except hydrogen; or $R_2$ is a group of the formula (I-a), (I-b) or (I-c);

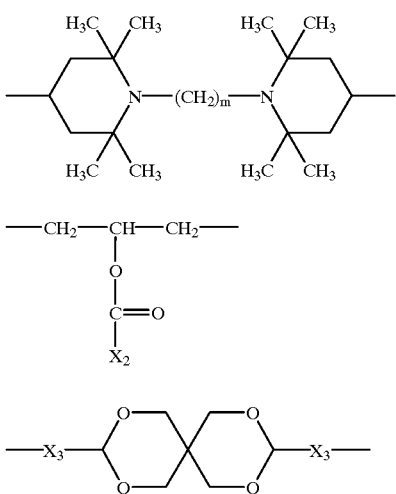

(I-a)

(I-b)

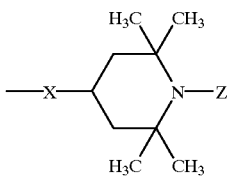

(I-c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

A is —$OR_3$, —$N(R_4)(R_5)$ or a group of the formula (II-1);

(II-1)

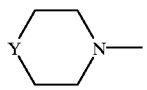

$R_3$, $R_4$ and $R_5$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

(III)

with Y being —O—, —$CH_2$—, —$CH_2CH_2$— or >N—$CH_3$, or —$N(R_4)(R_5)$ is additionally a group of the formula (III);

X is —O— or >N—$R_6$;

$R_6$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (IV-1), (IV-1)

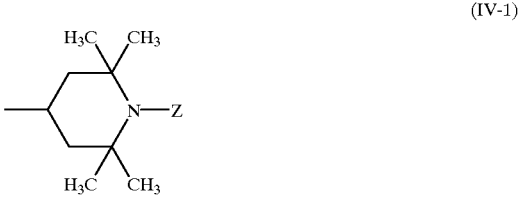

or $C_2$–$C_4$alkyl which is substituted in the 2, 3 or 4 position by —OH, $C_1$–$C_8$alkoxy, di($C_1$–$C_4$alkyl) amino or a group of the formula (III);

R has one of the meanings given for $R_6$; and

B has one of the meanings given for A.

26. A product according to claim 25 wherein Z is hydrogen.

27. A product according to claim 25 wherein $R_4$, $R_5$ and $R_6$ are different from hydrogen.

28. A product according to claim 25, having a polydispersity $\overline{Mw}/\overline{Mn}$ of 1.1 to 1.7.

29. A mixture containing a monodispers compound of the formula (M-I-a), a monodispers compound of the formula (M-I-a) and a monodispers compound of the formula (M-III-a), said compounds differing only in the number of the repetitive units, (M-I-a)

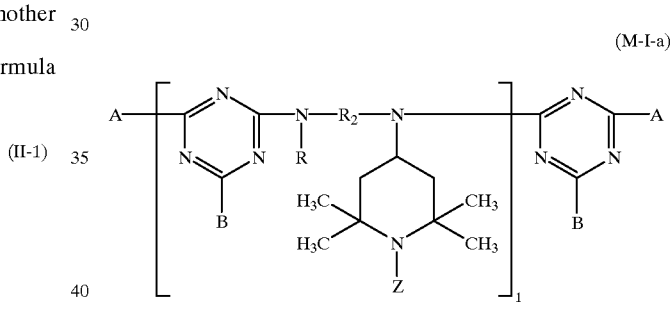

(M-II-a)

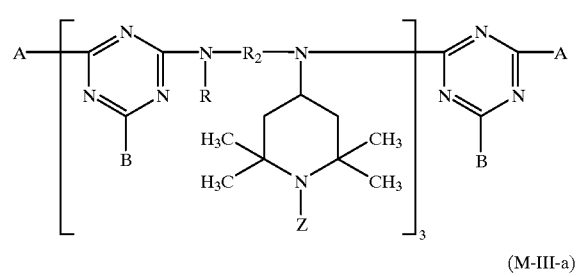

(M-III-a)

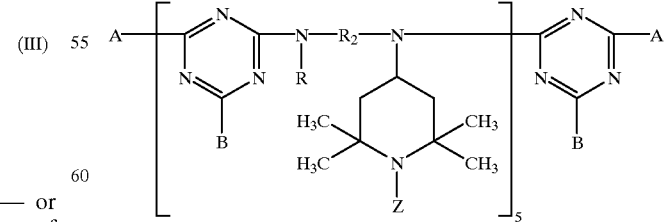

the radicals A, B, R, Z and $R_2$ being as defined in claim 25 and the total amount of the compound of the formula (M-I-a) being 15 to 45 mol %, the total amount of the compound of the formula (M-II-a) being 15 to 35 mol % and the total amount of the compound of the formula (M-III-a) being 3 to 18 mol %, relative to the total mixture (=N100 mol %).

30. A mixture according to claim 29 wherein

Z is hydrogen or $C_1$–$C_4$alkyl;
$R_2$ is $C_2$–$C_6$alkylene;
R is a group of the formula (IV-1);

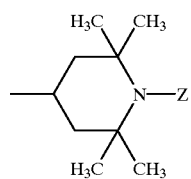

(IV-1)

A is —N($R_4$)($R_5$);
$R_4$ and $R_5$, which are identical or different, are $C_1$–$C_8$alkyl; B is a group of the formula (II-1);

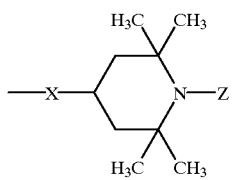

(II-1)

X is >$NR_6$;
$R_6$ is $C_1$–$C_8$alkyl.

31. A mixture according to claim 30 wherein

Z is hydrogen;
$R_2$ is hexamethylene;
$R_4$, $R_5$ and $R_6$ are butyl.

* * * * *